(12) United States Patent
Robichaux et al.

(10) Patent No.: US 11,446,302 B2
(45) Date of Patent: Sep. 20, 2022

(54) COMPOUNDS WITH ANTI-TUMOR ACTIVITY AGAINST CANCER CELLS BEARING EGFR OR HER2 EXON 20 MUTATIONS

(71) Applicant: Board of Regents, The University of Texas System, Austin, TX (US)

(72) Inventors: Jacqulyne Robichaux, Houston, TX (US); Monique Nilsson, Houston, TX (US); John V. Heymach, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 113 days.

(21) Appl. No.: 16/461,992

(22) PCT Filed: Nov. 17, 2017

(86) PCT No.: PCT/US2017/062326
§ 371 (c)(1),
(2) Date: May 17, 2019

(87) PCT Pub. No.: WO2018/094225
PCT Pub. Date: May 24, 2018

(65) Prior Publication Data
US 2020/0316071 A1 Oct. 8, 2020

Related U.S. Application Data

(60) Provisional application No. 62/572,716, filed on Oct. 16, 2017, provisional application No. 62/427,692, filed on Nov. 29, 2016, provisional application No. 62/423,732, filed on Nov. 17, 2016.

(51) Int. Cl.
*A61K 31/517* (2006.01)
*A61P 35/00* (2006.01)
*C12Q 1/6886* (2018.01)
*A61K 45/06* (2006.01)

(52) U.S. Cl.
CPC ............ *A61K 31/517* (2013.01); *A61P 35/00* (2018.01); *C12Q 1/6886* (2013.01); *A61K 45/06* (2013.01); *C12Q 2600/106* (2013.01); *C12Q 2600/156* (2013.01)

(58) Field of Classification Search
CPC ................ A61K 31/517; C12Q 1/6886; C12Q 2600/156; A61P 35/00
See application file for complete search history.

(56) References Cited

U.S. PATENT DOCUMENTS

2002/0177601 A1  11/2002  Himmelsbach et al.
2005/0085495 A1  4/2005  Soyka et al.
2006/0178364 A1  8/2006  Jung et al.
2007/0043009 A1  2/2007  Hennequin et al.

2011/0142929 A1  6/2011  Messerschmid et al.
2014/0112962 A1  4/2014  Kim et al.
2015/0307947 A1  10/2015  Basu et al.

FOREIGN PATENT DOCUMENTS

| EC | 03-4464 | 3/2003 |
| EC | 03-4646 | 7/2003 |
| EC | 06-6509 | 10/2006 |
| EC | 07-7645 | 8/2007 |
| EC | 10-10650 | 12/2010 |
| EC | 14-13121 | 2/2014 |
| WO | WO 2002/018351 | 3/2002 |

OTHER PUBLICATIONS

Han et al. (2017) A Phase II Study of Poziotinib in Patients with Epidermal Growth Factor Receptor (EGFR)-Mutant Lung Adenocarcinoma Who Have Acquired Resistance to EGFR-Tyrosine Kinase Inhibitors. Cancer Research Treatment, 49(1):10-19 (Year: 2017).*

Cha et al. (2012) Antitumor activity of HM781-36B, a highly effective pan-HER inhibitor in erlotinib-resistant NSCLC and other EGFR-dependent cancer models. International Journal of Cancer, 130:2445-2454 (Year: 2012).*

Hirano et al. (2015) In vitro modeling to determine mutation specificity of EGFR tyrosine kinase inhibitors against clinically relevant EGFR mutants in non-small-cell lung cancer. Oncotarget, 6(36):38789-38803 (Year: 2015).*

Kobayashi et al. (2016) Not all epidermal growth factor receptor mutations in lung cancer are created equal: Perspectives for individualized treatment strategy. Cancer Science, 107(9):1179-1186 (Year: 2016).*

Papadimitrakopoulou et al. (2012) Everolimus and Erlotinib as Second- or Third-Line Therapy in Patients with Advanced Non-Small-Cell Lung Cancer. Journal of Thoracic Oncology, 7:1594-1601 (Year: 2012).*

Cretella et al. (2014) Trastuzumab emtansine is active on HER-2 overexpressing NSCLC cell lines and overcomes gefitinib resistance. Molecular Cancer, 13(143):pp. 1-12 (Year: 2014).*

Nam et al., "Antitumor activity of HM781-36B, an irreversible Pan-HER inhibitor, alone or in combination with cytotoxic chemotherapeutic agents in gastric cancer," *Cancer Lett.*, 302(2):155-165, 2011.

Office Action issued in Chilean Office Action 2019-001353, dated Apr. 20, 2021.

Arcila et al., "EGFR Exon 20 Insertion Mutations in Lung Adenocarcinomas: Prevalence, Molecular Heterogeneity, and Clinicopathologic Characteristics," *Mol Cancer Ther.*, 12(2):220-229, 2013.

Arcila et al., "Prevalence, Clinicopathologic Associations, and Molecular Spectrum of ERBB2 (HER2) Tyrosine Kinase Mutations in Lung Adenocarcinomas," *Clin Cancer Res.*, 18(18):4910-4918, 2012.

(Continued)

*Primary Examiner* — Neil P Hammell
(74) *Attorney, Agent, or Firm* — Parker Highlander PLLC

(57) ABSTRACT

The present disclosure provides methods of treating cancer in a patient determined to have an EGFR and/or HER2 exon 20 mutation, such as an insertion mutation, by administering a third-generation tyrosine kinase inhibitor, such as poziotinib or afatinib.

18 Claims, 9 Drawing Sheets
Specification includes a Sequence Listing.

(56) References Cited

OTHER PUBLICATIONS

Besse et al., "Neratinib (N) with or without Temsirolimus (TEM) in Patients (PTS) with Non-Small Cell Lung Cancer (NSCLC) carrying HER2 Somatic mutations: An International Randomized Phase II Study," *Annals of Oncology*, 25(Suppl 4), Abstract LBA39_PR, 2014.

Cha et al., "Antitumor activity of HM781-36B, a highly effective pan-HER inhibitor in erlotinib-resistant NSCLC and other EGFR-dependent cancer models," *Int. J. Cancer*, 130:2445-2454, 2012.

Cho et al., "Cetuximab response of lung cancer-derived EGF receptor mutants is associated with asymmetric dimerization," *Cancer Res.*, 73(22):6770-6779, 2013.

Costa et al., "Pulse Afatinib for ERBB2 Exon 20 Insertion-Mutated Lung Adenocarcinomas," *J Thorac Oncol.*, 11(6):918-923, 2016.

Elamin et al., "Preliminary results of a phase II study of poziotinib in EGFR exon 20 mutant advanced NSCLC," *J Thor Oncol*, 12(8S):1536, 2017.

Han et al., "A Phase II Study of Poziotinib in Patients with Epidermal Growth Factor Receptor (EGFR)-Mutant Lung Adenocarcinoma Who Have Acquired Resistance to EGFR-Tyrosine Kinase Inhibitors," *Cancer Res Treat*, 49(1):10-19, 2017.

Kobayashi et al., "Not all epidermal growth factor receptor mutations in lung cancer are created equal: Perspectives for individualized treatment strategy," *Cancer Sci*, 107(9):1179-1186, 2016.

Kosaka et al., "Response Heterogeneity of EGFR and HER2 Exon 20 Insertions to Covalent EGFR and HER2 Inhibitors," *Cancer Res*, 77(10):2712-2721, 2017.

Maemondo et al., "Gefitinib or Chemotherapy for Non-Small-Cell Lung Cancer with Mutated EGFR," *N Engl J Med*, 362:2380-2388, 2010.

Mazieres et al., "Lung cancer that harbors an HER2 mutation: epidemiologic characteristics and therapeutic perspectives," *Journal of Clinical Oncology*, 31(16):1997-2003, 2013.

Opposition filed in Ecuadoran Application No. 2019-43254, dated Feb. 5, 2020 (English translation).

Partial Supplementary European Search Report issued in European Application No. 17871141.2, dated May 29, 2020.

PCT International Search Report and Written Opinion issued in International Application PCT/US2017/062326, dated Mar. 29, 2018.

Perera et al., "HER2YVMA Drives Rapid Development of Adenosquamous Lung Tumors in Mice That Are Sensitive to BIBW2992 and Rapamycin Combination Therapy," *Proc Natl Acad Sci U S A*, 106(2):474-479, 2009.

Robichaux et al., "Inhibition of HER2 mutant non-small cell lung cancer using 3rd generation EGFR/HER2 inhibitors," *Cancer Res*, 76(14 Supplement):4799, 2016.

Robichaux et al., "MA16.07 Drug Repurposing to Overcome De Novo Resistance of Non-Traditional EGFR Mutations," *Journal of Thoracic Oncology*, 12(1):S438, 2017.

Suzawa et al. "Antitumor effect of afatinib, as a human epidermal growth factor receptor 2- targeted therapy, in lung cancers harboring HER2 oncogene alterations," *Cancer Science*, 107(1)45-52, 2016.

Thress et al., "Acquired EGFR C797S mutation mediates resistance to AZD9291 in non-small cell lung cancer harboring EGFR T790M," *Nat Med.*, 21(6):560-562, 2015.

Yang et al., "Clinical activity of afatinib in patients with advanced non-small-cell lung cancer harbouring uncommon EGFR mutations: a combined post-hoc analysis of LUX-Lung 2, LUX-Lung 3, and LUX-Lung 6," *Lancet Oncol*, 16:830-838, 2015.

Yang et al., "NSCLC harboring EGFR exon—20 insertions after the regulatory C—helix of kinase domain responds poorly to known EGFR inhibitors," *Int. J. Cancer*, 139:171-176, 2016.

Yasuda et al., "EGFR exon 20 insertion mutations in non-small-cell lung cancer: preclinical data and clinical implications," *Lancet Oncol*, 13:e23-31, 2012.

Mitsudomi et al., "Commentary on EGFR gene mutation examination in lung cancer patients," EGFR commentary committee of the Japan Lung Cancer Society, issue 1.7, pp. i-xviii, May 11, 2009, and partial English translation.

Office Action issued in Japanese Application No. 2019-526282, dated Dec. 8, 2021, and English language translation thereof.

Yamada et al., "Mechanisms of tumor resistance to EGFR-targeted therapies," *Nippon Kinsho*, 71(Suppl. 6):258-262, 2013. (Japanese).

Yasuda et al., "Structural, biochemical, and clinical characterization of epidermal growth factor receptor (EGFR) exon 20 insertion mutations in lung cancer," *Sci Transl Med.*, 5(216):1-23, 2013.

* cited by examiner

SEQUENCE LISTING

```
<160> NUMBER OF SEQ ID NOS: 18

<210> SEQ ID NO 1
<211> LENGTH: 4
<212> TYPE: PRT
<213> ORGANISM: Artificial Sequence
<220> FEATURE:
<223> OTHER INFORMATION: EGFR mutation

<400> SEQUENCE: 1

Phe Gln Glu Ala
1

<210> SEQ ID NO 2
<211> LENGTH: 12
<212> TYPE: DNA
<213> ORGANISM: Artificial Sequence
<220> FEATURE:
<223> OTHER INFORMATION: EGFR mutation

<400> SEQUENCE: 2
tccaggaagc ct                                                              12

<210> SEQ ID NO 3
<211> LENGTH: 4
<212> TYPE: PRT
<213> ORGANISM: Artificial Sequence
<220> FEATURE:
<223> OTHER INFORMATION: HER2 mutation

<400> SEQUENCE: 3

Tyr Val Met Ala
1

<210> SEQ ID NO 4
<211> LENGTH: 12
<212> TYPE: DNA
<213> ORGANISM: Artificial Sequence
<220> FEATURE:
<223> OTHER INFORMATION: HER2 mutation

<400> SEQUENCE: 4
tatgtcatgg ct                                                              12

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
cttacaccca gtggagaagc                                                      20

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
accaagcgac ggtcctccaa                                                      20

<210> SEQ ID NO 7
<211> LENGTH: 45
```

```
<212> TYPE: DNA
<213> ORGANISM: Homo sapiens

<400> SEQUENCE: 7
gaagcctacg tgatggccag cgtggacaac ccccacgtgt gccgc           45

<210> SEQ ID NO 8
<211> LENGTH: 66
<212> TYPE: DNA
<213> ORGANISM: Artificial Sequence
<220> FEATURE:
<223> OTHER INFORMATION: EGFR exon 20 A763insFQEA

<400> SEQUENCE: 8
gaagcctcca ggaagcctta cgtgatggcc agcagcgtgg acgtggacaa ccccacgtg    60 tgccgc                                                              66

<210> SEQ ID NO 9
<211> LENGTH: 45
<212> TYPE: DNA
<213> ORGANISM: Artificial Sequence
<220> FEATURE:
<223> OTHER INFORMATION: EGFR exon 20 S768dupSVD

<400> SEQUENCE: 9
gaagcctacg tgatggccag cgtggacaac ccccacgtgt gccgc           45

<210> SEQ ID NO 10
<211> LENGTH: 54
<212> TYPE: DNA
<213> ORGANISM: Artificial Sequence
<220> FEATURE:
<223> OTHER INFORMATION: EGFR exon 20 V769insASV

<400> SEQUENCE: 10
gaagcctacg tgatggccag cgtgccagcg tgggacaacc cccacgtgtg ccgc         54

<210> SEQ ID NO 11
<211> LENGTH: 54
<212> TYPE: DNA
<213> ORGANISM: Artificial Sequence
<220> FEATURE:
<223> OTHER INFORMATION: EGFR exon 20 D770insSVD

<400> SEQUENCE: 11
gaagcctacg tgatggccag cgtggacgcg tggacaaacc cccacgtgtg ccgc         54

<210> SEQ ID NO 12
<211> LENGTH: 54
<212> TYPE: DNA
<213> ORGANISM: Artificial Sequence
<220> FEATURE:
<223> OTHER INFORMATION: EGFR exon 20 H773insNPH

<400> SEQUENCE: 12
gaagcctacg tgatggccag cgtggacaac ccccacaacc cccacgtgtg ccgc         54

<210> SEQ ID NO 13
<211> LENGTH: 48
<212> TYPE: DNA
<213> ORGANISM: Homo sapiens

<400> SEQUENCE: 13
gaagcatacg tgatggctgg tgtgggctcc ccatatgtct cccgcctt             48
```

```
<210> SEQ ID NO 14
<211> LENGTH: 48
<212> TYPE: DNA
<213> ORGANISM: Artificial Sequence
<220> FEATURE:
<223> OTHER INFORMATION: HER2 exon 20 G776V

<400> SEQUENCE: 14
gaagcatacg tgatggctgt tgtgggctcc ccatatgtct cccgcctt          48

<210> SEQ ID NO 15
<211> LENGTH: 51
<212> TYPE: DNA
<213> ORGANISM: Artificial Sequence
<220> FEATURE:
<223> OTHER INFORMATION: HER2 exon 20 G776V V777insV

<400> SEQUENCE: 15
gaagcatacg tgatggcttg tgtgttgggc tccccatatg tctcccgcct t      51

<210> SEQ ID NO 16
<211> LENGTH: 51
<212> TYPE: DNA
<213> ORGANISM: Artificial Sequence
<220> FEATURE:
<223> OTHER INFORMATION: HER2 exon 20 G776del insVV

<400> SEQUENCE: 16
gaagcatacg tgatggctgt tgttgtgggc tccccatatg tctcccgcct t      51

<210> SEQ ID NO 17
<211> LENGTH: 52
<212> TYPE: DNA
<213> ORGANISM: Artificial Sequence
<220> FEATURE:
<223> OTHER INFORMATION: HER2 exon 20 G776del ins V

<400> SEQUENCE: 17
cgaagcatac gtgatggctg gtgtgtctgg ctccccatat gtctcccgcc tt     52

<210> SEQ ID NO 18
<211> LENGTH: 57
<212> TYPE: DNA
<213> ORGANISM: Artificial Sequence
<220> FEATURE:
<223> OTHER INFORMATION: HER2 exon P780insGSP

<400> SEQUENCE: 18
gaagcatacg tgatggctgg tgtgggctcc ccatggctcc cctatgtctc ccgcctt    57
```

COMPOUNDS WITH ANTI-TUMOR ACTIVITY AGAINST CANCER CELLS BEARING EGFR OR HER2 EXON 20 MUTATIONS

This application is a national phase application under 35 U.S.C. § 371 of International Application No. PCT/US2017/062326, filed Nov. 17, 2017, which claims the benefit of U.S. Provisional Patent Application No. 62/423,732, filed Nov. 17, 2016, U.S. provisional application No. 62/427,692, filed Nov. 29, 2016, and U.S. provisional application No. 62/572,716, filed Oct. 16, 2017 the entire contents of each of which are incorporated herein by reference.

The invention was made with government support under grant number CA190628 awarded by the National Institutes of Health. The government has certain rights in the invention.

The sequence listing that is contained in the file named "UTSCP1306US.txt", which is 4 KB (as measured in Microsoft Windows) and was created on May 16, 2019, is filed herewith by electronic submission and is incorporated by reference herein.

BACKGROUND

1. Field of the Invention

The present invention relates generally to the field of molecular biology and medicine. More particularly, it concerns methods of treating patients with EGFR and/or HER2 exon 20 mutations, such as insertion mutations.

2. Description of Related Art

Approximately 10-15% of NSCLCs harbor activating EGFR mutations. For the majority of these patients whose tumors have "classical" sensitizing mutations (L858R and exon 19 deletions), TKIs such as gefitinib and erlotinib provide dramatic clinical benefit, with approximately 70% experiencing objective responses (OR), improved progression free survival (PFS), and quality of life compared to chemotherapy alone (Maemondo et al., 2010). However, approximately 10-12% of EGFR mutant NSCLC tumors have an in-frame insertion within exon 20 of EGFR (Arcila et al., 2012), and are generally resistant to EGFR TKIs. In addition, 90% of HER2 mutations in NSCLC are exon 20 mutations (Mazieres et al., 2013). Together, EGFR and HER2 exon 20 mutations comprise approximately 4% of NSCLC patients. The data thus far suggests that available TKIs of HER2 (afatinib, lapatinib, neratinib, dacomitinib) have limited activity in patients with HER2 mutant tumors with many studies reporting OR rates below 40% (Kosaka et al., 2017), although some preclinical activity is observed in HER2 mouse models treated with afatinib (Perera et al., 2009).

Exon 20 of EGFR and HER2 contains two major regions, the c-helix (residues 762-766 in EGFR and 770-774 in HER2) and the loop following the c-helix (residues 767-774 in EGFR and 775-783 in HER2). Crystallography of the EGFR exon 20 insertion D770insNPG has revealed a stabilized and ridged active conformation inducing resistance to first generation TKIs in insertions after residue 764. However, modeling of EGFR A763insFQEA demonstrated that insertions before residue 764 do not exhibit this effect and do not induce drug resistance (Yasuda et al., 2013). Moreover, in a patient derived xenograft (PDX) model of EGFR exon 20 driven NSCLC where insertions are in the loop after the c-helix (EGFR H773insNPH), third generation EGFR TKIs, osimertinib (AZD9291) and rociletinib (CO-1696) were found to have minimal activity (Yang et al., 2016). In a recent study of rare EGFR and HER2 exon 20 mutations, the authors found a heterogeneous response to covalent quinazoline-based second generation inhibitors such as dacomitinib and afatinib; however, concentrations required to target more common exon 20 insertion mutations were above clinically achievable concentrations (Kosaka et al., 2017). Therefore, there is a significant clinical need to identify novel therapies to overcome the innate drug resistance of NSCLC tumors harboring exon 20 mutations, particularly insertion mutations, in EGFR and HER2.

SUMMARY

The present disclosure provides methods and compositions for treating cancer in patients with EGFR and/or HER2 exon 20 mutations, such as exon 20 insertion mutations. In one embodiment, there is provided a method of treating cancer in a subject comprising administering an effective amount of poziotinib to the subject, wherein the subject has been determined to have one or more EGFR exon 20 mutations, such as one or more EGFR exon 20 insertion mutations. In particular aspects, the subject is human.

In certain aspects, the one or more EGFR exon 20 mutations comprise one or more point mutations, insertions, and/or deletions of 3-18 nucleotides between amino acids 763-778. In some aspects, the subject has been determined to have 2, 3, or 4 EGFR exon 20 mutations. In some aspects, the one or more EGFR exon 20 mutations are at one or more residues selected from the group consisting of A763, A767, S768, V769, D770, N771, P772, and H773. In certain aspects, the subject has been determined to not have an EGFR mutation at residue C797. In some aspects, the one or more exon 20 mutations are selected from the group consisting of A763insFQEA, A767insASV, S768dupSVD, V769insASV, D770insSVD, D770insNPG, H773insNPH, N771del insGY, N771del insFH, and N771dupNPH.

In certain aspects, the subject was determined to have an EGFR exon 20 mutation, such as an insertion mutation, by analyzing a genomic sample from the subject. In some aspects, the genomic sample is isolated from saliva, blood, urine, normal tissue, or tumor tissue. In particular aspects, the presence of an EGFR exon 20 mutation is determined by nucleic acid sequencing (e.g., DNA sequencing of tumor tissue or circulating free DNA from plasma) or PCR analyses.

In certain aspects, the method further comprises administering an additional anti-cancer therapy. In some aspects, the anti-cancer therapy is chemotherapy, radiotherapy, gene therapy, surgery, hormonal therapy, anti-angiogenic therapy or immunotherapy. In certain aspects, the poziotinib and/or anti-cancer therapy are administered intravenously, subcutaneously, intraosseously, orally, transdermally, in sustained release, in controlled release, in delayed release, as a suppository, or sublingually. In some aspects, administering the poziotinib and/or anti-cancer therapy comprises local, regional or systemic administration. In particular aspects, the poziotinib and/or anti-cancer therapy are administered two or more times, such as daily, every other day, or weekly.

In some aspects, the cancer is oral cancer, oropharyngeal cancer, nasopharyngeal cancer, respiratory cancer, urogenital cancer, gastrointestinal cancer, central or peripheral nervous system tissue cancer, an endocrine or neuroendocrine cancer or hematopoietic cancer, glioma, sarcoma, carcinoma, lymphoma, melanoma, fibroma, meningioma, brain cancer, oropharyngeal cancer, nasopharyngeal cancer, renal cancer, biliary cancer, pheochromocytoma, pancreatic islet cell cancer, Li-Fraumeni tumors, thyroid cancer, parathyroid cancer, pituitary tumors, adrenal gland tumors, osteogenic sarcoma tumors, multiple neuroendocrine type I and type II tumors, breast cancer, lung cancer, head and neck cancer, prostate cancer, esophageal cancer, tracheal cancer, liver cancer, bladder cancer, stomach cancer, pancreatic cancer, ovarian cancer, uterine cancer, cervical cancer, testicular cancer, colon cancer, rectal cancer or skin cancer. In particular aspects, the cancer is non-small cell lung cancer.

In another embodiment, there is provided a pharmaceutical composition comprising poziotinib for a patient determined to have one or more EGFR exon 20 mutations, such as one or more EGFR exon 20 insertion mutations. In certain aspects, the one or more EGFR exon 20 mutations comprise a point mutation, insertion, and/or deletion of 3-18 nucleotides between amino acids 763-778. In certain aspects, the subject has been determined to have 2, 3, or 4 EGFR exon 20 mutations.

In some aspects, the one or more EGFR exon 20 insertion mutations are at one or more residues selected from the group consisting of A763, A767, S768, V769, D770, N771, P772, and H773. In certain aspects, the subject has been determined to not have an EGFR mutation at residue C797. In particular aspects, the one or more exon 20 mutations are selected from the group consisting of A763insFQEA, A767insASV, S768dupSVD, V769insASV, D770insSVD, D770insNPG, H773insNPH, N771del insGY, N771del insFH, and N771dupNPH. In some aspects, the patient is being treated with an anti-cancer therapy.

In yet another embodiment, there is provided a method of predicting a response to poziotinib alone or in combination with an anti-cancer therapy in a subject having a cancer comprising detecting an EGFR exon 20 mutation (e.g., EGFR exon 20 insertion mutation) in a genomic sample obtained from said patient, wherein if the sample is positive for the presence of the EGFR exon 20 mutation, then the patient is predicted to have a favorable response to poziotinib alone or in combination with an anti-cancer therapy. In some aspects, the genomic sample is isolated from saliva, blood, urine, normal tissue, or tumor tissue. In certain aspects, the presence of an EGFR exon 20 mutation is determined by nucleic acid sequencing or PCR analyses. In certain aspects, the EGFR exon 20 mutation comprises one or more point mutations, insertions, and/or deletions of 3-18 nucleotides between amino acids 763-778. In some aspects, the EGFR exon 20 mutation is at residue A763, H773, A767, S768, V769, D770, N771, and/or D773. In some aspects, the EGFR exon 20 mutation is selected from the group consisting of A763insFQEA, A767insASV, S768dupSVD, V769insASV, D770insSVD, D770insNPG, H773insNPH, N771del insGY, N771del insFH and N771dupNPH. In certain aspects, a favorable response to poziotinib inhibitor alone or in combination with an anti-cancer therapy comprises reduction in tumor size or burden, blocking of tumor growth, reduction in tumor-associated pain, reduction in cancer associated pathology, reduction in cancer associated symptoms, cancer non-progression, increased disease free interval, increased time to progression, induction of remission, reduction of metastasis, or increased patient survival. In further aspects, the patient predicted to have a favorable response is administered poziotinib alone or in combination with a second anti-cancer therapy.

A further embodiment provides a method of treating cancer in a patient comprising administering an effective amount of poziotinib or afatinib to the subject, wherein the subject has been determined to have one or more HER2 exon 20 mutations selected from the group consisting of A775insV G776C, A775insYVMA, G776C V777insC, G776del insVV, G776del insVC, and P780insGSP. In some aspects, the one or more HER2 exon 20 mutations further comprise one or more point mutations, insertions, and/or deletions of 3-18 nucleotides between amino acids 770-785. In some aspects, the one or more HER2 exon 20 mutations are at residue A775, G776, S779, and/or P780. In particular aspects, the subject is human.

In some aspects, the method further comprises administering an mTOR inhibitor. In certain aspects, the mTOR inhibitor is rapamycin, temsirolimus, everolimus, ridaforolimus or MLN4924. In particular aspects, the mTOR inhibitor is everolimus.

In certain aspects, the poziotinib or afatinib and/or mTOR inhibitor are administered intravenously, subcutaneously, intraosseously, orally, transdermally, in sustained release, in controlled release, in delayed release, as a suppository, or sublingually. In some aspects, the patient was determined to have a HER2 exon 20 mutation by analyzing a genomic sample from the patient. In certain aspects, the genomic sample is isolated from saliva, blood, urine, normal tissue, or tumor tissue. In some aspects, the presence of an HER2 exon 20 mutation is determined by nucleic acid sequencing or PCR analyses.

In additional aspects, the method further comprises administering an additional anti-cancer therapy. In some aspects, the anti-cancer therapy is chemotherapy, radiotherapy, gene therapy, surgery, hormonal therapy, anti-angiogenic therapy or immunotherapy.

In some aspects, the cancer is oral cancer, oropharyngeal cancer, nasopharyngeal cancer, respiratory cancer, urogenital cancer, gastrointestinal cancer, central or peripheral nervous system tissue cancer, an endocrine or neuroendocrine cancer or hematopoietic cancer, glioma, sarcoma, carcinoma, lymphoma, melanoma, fibroma, meningioma, brain cancer, oropharyngeal cancer, nasopharyngeal cancer, renal cancer, biliary cancer, pheochromocytoma, pancreatic islet cell cancer, Li-Fraumeni tumors, thyroid cancer, parathyroid cancer, pituitary tumors, adrenal gland tumors, osteogenic sarcoma tumors, multiple neuroendocrine type I and type II tumors, breast cancer, lung cancer, head and neck cancer, prostate cancer, esophageal cancer, tracheal cancer, liver cancer, bladder cancer, stomach cancer, pancreatic cancer, ovarian cancer, uterine cancer, cervical cancer, testicular cancer, colon cancer, rectal cancer or skin cancer. In certain aspects, the cancer is non-small cell lung cancer.

In another embodiment, there is provided a pharmaceutical composition comprising poziotinib or afatinib for a patient determined to have one or more HER2 exon 20 mutations selected from the group consisting of A775insV G776C, A775insYVMA, G776C V777insC, G776del insVV, G776del insVC, and P780insGSP. In some aspects, the HER2 exon 20 mutation further comprises one or more point mutations, insertions, and/or deletions of 3-18 nucleotides between amino acids 770-785. In some aspects, the HER2 exon 20 mutation is at residue A775, G776, S779, and/or P780. In some aspects, the patient is being treated with an anti-cancer therapy.

In yet another embodiment, there is provided a method of predicting a response to poziotinib or afatinib alone or in combination with an anti-cancer therapy in a patient having a cancer comprising detecting an HER2 exon 20 mutation (e.g., HER2 exon 20 insertion mutation) selected from the group consisting of A775insV G776C, A775insYVMA, G776C V777insC, G776del insVV, G776del insVC, and P780insGSP in a genomic sample obtained from said patient, wherein if the sample is positive for the presence of the HER2 exon 20 mutation, then the patient is predicted to have a favorable response to the poziotinib or afatinib alone or in combination with an anti-cancer therapy. In some aspects, the HER2 exon 20 mutation further comprises one or more point mutations, insertions, and/or deletions of 3-18 nucleotides between amino acids 770-785. In certain aspects, the HER2 exon 20 mutation is at residue A775, G776, S779, and/or P780.

In some aspects, the genomic sample is isolated from saliva, blood, urine, normal tissue, or tumor tissue. In certain aspects, the presence of a HER2 exon 20 mutation is determined by nucleic acid sequencing or PCR analyses. In particular aspects, the anti-cancer therapy is an mTOR inhibitor. In some aspects, a favorable response to poziotinib or afatinib inhibitor alone or in combination with an anti-cancer therapy comprises reduction in tumor size or burden, blocking of tumor growth, reduction in tumor-associated pain, reduction in cancer associated pathology, reduction in cancer associated symptoms, cancer non-progression, increased disease free interval, increased time to progression, induction of remission, reduction of metastasis, or increased patient survival. In further aspects, the patient predicted to have a favorable response is administered poziotinib alone or in combination with a second anti-cancer therapy.

Also provided herein is a composition comprising nucleic acids isolated from human cancer cells; and a primer pair that can amplify at least a first portion of exon 20 of a human EGFR or HER2 coding sequence. In some aspects, the composition further comprises a labeled probe molecule that can specifically hybridize to the first portion of exon 20 of the human EGFR or HER coding sequence when there is a mutation in the sequence. In certain aspects, the composition further comprises a thermostable DNA polymerase. In some aspects, the composition further comprises dNTPS. In some aspects, the labeled probe hybridizes to the first portion of exon 20 of the human EGFR coding sequence when there is a mutation selected from the group consisting of A763insFQEA, A767insASV, S768dupSVD, V769insASV, D770insSVD, D770insNPG, H773insNPH, N771del insGY, N771del insFH, and N771dupNPH. In certain aspects, the labeled probe hybridizes to the first portion of exon 20 of the human HER2 coding sequence when there is a mutation selected from the group consisting of A775insV G776C, A775insYVMA, G776V, G776C V777insV, G776C V777insC, G776del insVV, G776del insVC, and P780insGSP.

In another embodiment, there is provided an isolated nucleic acid encoding a mutant EGFR protein, wherein said mutant protein differs from wild-type human EGFR by one or more EGFR exon 20 mutations comprising a point mutation, insertion, and/or deletion of 3-18 nucleotides between amino acids 763-778. In some aspects, the one or more EGFR exon 20 mutations are at one or more residues selected from the group consisting of A763, A767, S768, V769, D770, N771, P772, and H773. In certain aspects, the one or more exon 20 mutations are selected from the group consisting of A763insFQEA, A767insASV, S768dupSVD, V769insASV, D770insSVD, D770insNPG, H773insNPH, N771del insGY, N771del insFH, and N771dupNPH. In specific aspects, the nucleic acid comprises the sequence of SEQ ID NO:8, 9, 10, 11, or 12.

In yet another embodiment, there is provided an isolated nucleic acid encoding a mutant HER2 protein, wherein said mutant protein differs from wild-type human HER2 by one or more HER2 exon 20 mutations comprising one or more point mutations, insertions, and/or deletions of 3-18 nucleotides between amino acids 770-785. In some aspects, the one or more HER2 exon 20 mutations are at residue A775, G776, S779, and/or P780. In certain aspects, the one or more HER2 exon 20 mutations selected from the group consisting of A775insV G776C, A775insYVMA, G776V, G776C V777insV, G776C V777insC, G776del insVV, G776del insVC, and P780insGSP. In specific aspects, the nucleic acid comprises the sequence of SEQ ID NO:14, 15, 16, 17, or 18.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 1A) Progression free survival (PFS) of patients with classical and exon 20 EGFR mutations demonstrates resistance to first line therapy. Patients with exon 20 insertions have decreased percent survival. (FIG. 1B) Schematic of EGFR and HER2 exon 20 insertion mutations generated in stable Ba/F3 model. Dose response curves of cell viability of Ba/F3 cell lines expressing EGFR (FIGS. 1C-E) and (FIGS. 1F-H) HER2 exon 20 insertion mutations treated with 1st, 2nd, and 3rd generation TKIs for 72 hours. (FIGS. 1C-H) The mean±SEM of 6 cell lines is plotted for each concentration (n=3). (FIG. 1I) 3-D modeling of EGFR D770insNPG and T790M. Shifts of the P-loop and the α-c-helix into the binding pocket result in steric hindrance, pushing AZD9291 out of the binding pocket. (FIG. 1J) 3-D modeling of HER2 A775insYVMA and WT. Overall shifts of the P-loop and the α-c-helix into the binding pocket result in an overall reduction in the size of the binding pocket.

(FIG. 2C) Western blotting confirms inhibition of p-EGFR and p-HER2 in Ba/F3 cell lines after 2 hours of poziotinib treatment (n=2). (FIG. 2D) Correlation of Ba/F3 EGFR exon 20 insertion location with amino acid location (n=2). Pearson correlation and p-value were determined using GraphPad Prism. (FIG. 2E) Dose response curves of cell viability of patient derived cell line CUTO14 expressing EGFR A767dupASV and (FIG. 2F) YUL0019 expressing EGFR N771del insFH treated with poziotinib or afatinib for 72 hours (n=3). (FIG. 2F) IC50 values of EGFR mutant Ba/F3 cells normalized to the IC50 values of Ba/F3 EGFR T790M cell line after incubation with afatinib, osimertinib, rociletinib, or poziotinib for 72 hours (n=3). (FIG. 2G) Bars are representative of mean±SEM. Values greater than 1 are indicative of less potent inhibition compared to T790M, whereas values less than one indicate more potent inhibition of exon 20 insertions compared to T790M.

(FIGS. 3A-B) Two-sided student's t-test was used to calculate p-value. Representative MRI images of EGFR (FIG. 3C) and HER2 (FIG. 3D) GEMM before and after 4 weeks poziotinib treatment demonstrate robust tumor regression. Plots of tumor volume of EGFR D770insNPG (FIG. 3E) (n=4) and HER2 A775insYVMA (FIG. 3F) (n=6) treated with 10 mg/kg of poziotinib 5 days/week for 12 weeks, exhibits mice continue to respond to poziotinib treatment. (FIG. 3G) YUL-0019 (EGFR N77 1delinsFH) cells treated with afatinib or poziotinib. The cells treated with 10 mg/kg poziotinib had the lowest tumor volume and with 5 mg/kg had the 2nd to lowest tumor volume. (FIG. 3H) EGFR H773insNPH PDX mice were treated with vehicle control (n=6), 5 mg/kg (n=6) or 10 mg/kg (n=3) of poziotinib. The mice treated with poziotinib had decreased tumor volume. Waterfall plots demonstrate that tumor burden was reduced by >85% in all poziotinib treated mice, and in 8 out of 9 poziotinib treated mice, xenografts were completely reduced to a residual bolus. One-way ANOVA analysis was used in combination with Tukey's test to determine statistical significance, ***, p<0.0001.

(FIG. 4A) Waterfall plots of individual patients with EGFR exon 20 insertions displays de novo resistance to erlotinib, geftinib, or afatinib. Patient mutations are listed below each representative bar. (FIG. 4B) Stable Ba/F3 cell lines expressing EGFR exon 20 insertion mutations are viable in IL-3 independent conditions, unlike Ba/F3 empty vector expressing cells or EGFR WT expressing Ba/F3 cells, indicating that EGFR exon 20 insertions are activating mutations. (FIG. 4C) IL-3 independent growth of 11 stable Ba/F3 cell lines expressing different HER2 mutations displays that the majority of HER2 activating mutations are within exon 20 of HER2. With the exception of L755P, all activating mutations were HER2 exon 20 insertion mutations. (FIGS. 4B-C) Cell viability was determined by the Cell Titer Glo assay. The mean±SEM is plotted for each cell line (n=3).

(FIG. 8A) Western blots of p-EGFR and p-HER2 after 2 hours of poziotinib treatment in indicated Ba/F3 cell lines were quantified using Photoshop. Values were plotted in Graphpad Prism and bars are representative of mean±SEM. (N=2) (FIG. 8B) Western blot of CUTO-14 patient derived cell line after 3 hours of indicated doses of afatinib or poziotinib (N=3). (FIG. 8C) Quantification of p-EGFR from western blots after 3 hours of indicated doses of afatinib or poziotinib in CUTO-14 cell line. Poziotinib treatment resulted in decreased p-EGFR. (FIG. 8D) Linear regression plot of IC50 values vs. relative expression of Ba/F3 cell lines demonstrated that there was no correlation between expression and sensitivity to poziotinib (n=2). (FIG. 8E) Linear regression plot of IC50 values vs. the location of the mutation within the HER2 receptor demonstrated that there was no correlation between location and sensitivity to poziotinib in HER2 mutant Ba/F3 cell lines (n=2). Pearson correlations and p-values were calculated using Graphpad prism. p<0.05 (*), p<0.01 () or p<0.001 (*).

DESCRIPTION OF ILLUSTRATIVE EMBODIMENTS

Figures 1A, 1B, 1C, 1D, 1E, 1F, 1G, 1H, 1I, 1J:
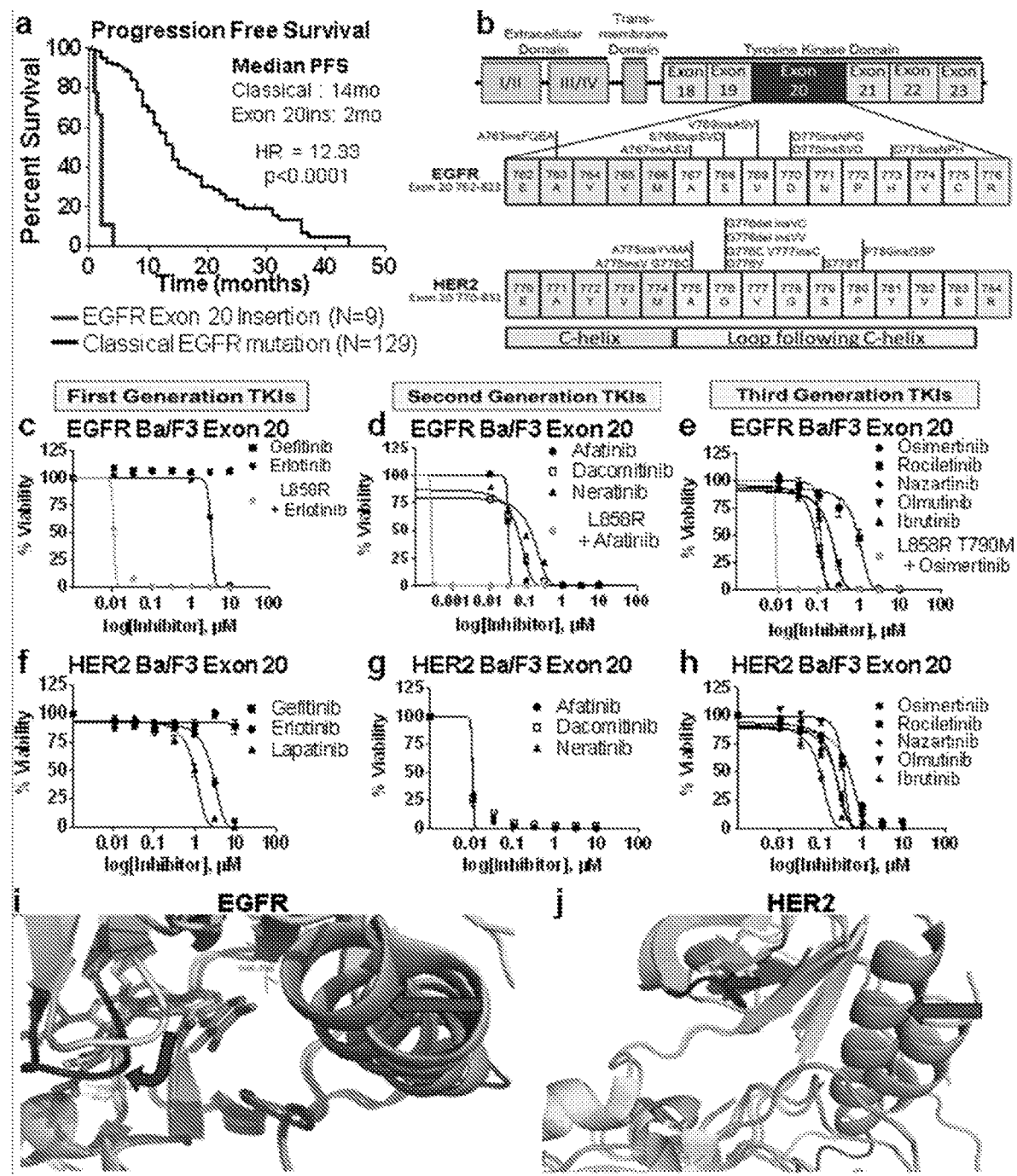
FIGS. 1A-1J: Exon 20 insertion mutations induce de novo resistance to covalent and non-covalent TKIs.

Although the majority of activating mutations of epidermal growth factor receptor (EGFR) mutant non-small cell lung cancers (NSCLCs) are sensitive to available EGFR tyrosine kinase inhibitor (TKIs), a subset with alterations in exon 20 of EGFR and HER2 are intrinsically resistant. The present studies utilized in silico, in vitro, and in vivo testing to model structural alterations induced by these exon 20 mutations and identify effective inhibitors. 3-D modeling revealed significant alterations restricting the size of the drug binding pocket, imposing the binding of large, rigid inhibitors. It was found that poziotinib, due to its small size and flexibility, was able to circumvent these steric changes, and is a potent and relatively selective inhibitor of the EGFR or HER2 exon 20 mutant proteins. Poziotinib also has potent activity in mutant exon 20 EGFR or HER2 NSCLC patient-derived xenograft (PDX) models and genetically engineered mouse models. Thus, these data identify poziotinib as a potent, clinically active inhibitor of EGFR/HER2 exon 20 mutations, and illuminate the molecular features of kinase inhibitors that may circumvent steric changes induced by these insertions.

Accordingly, certain embodiments of the present disclosure provide methods for treating cancer patients with EGFR and/or HER2 exon 20 mutations, such as exon 20 insertions. In particular, the present methods comprise the administration of poziotinib (also known as HM781-36B) or afatinib to patients identified to have EGFR and/or HER exon 20 insertion mutations. The size and flexibility of poziotinib overcomes steric hindrance, inhibiting EGFR and HER2 exon 20 mutants at low nanomolar concentrations. Thus, poziotinib or afatinib as well as structurally similar inhibitors are potent EGFR or HER2 inhibitors that can be used to target both EFGR and HER2 exon 20 insertions which are resistant to irreversible 2$^{nd}$ and 3$^{rd}$ generations TKIs.

I. DEFINITIONS

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease. For example, a treatment may include administration of an effective amount of poziotinib or afatinib.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human patients are adults, juveniles, infants and fetuses.

The term "effective," as that term is used in the specification and/or claims, means adequate to accomplish a desired, expected, or intended result. "Effective amount," "therapeutically effective amount" or "pharmaceutically effective amount" when used in the context of treating a patient or subject with a compound means that amount of the compound which, when administered to a subject or patient for treating or preventing a disease, is an amount sufficient to effect such treatment or prevention of the disease.

As used herein, the term "IC$_{50}$" refers to an inhibitory dose which is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half.

An "anti-cancer" agent is capable of negatively affecting a cancer cell/tumor in a subject, for example, by promoting killing of cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer.

The term "insertion(s)" or "insertion mutation(s)" refers to the addition of one or more nucleotide base pairs into a DNA sequence. For example, an insertion mutation of exon 20 of EGFR can occur between amino acids 767 to 774, of about 2-21 base pairs. In another example, HER2 exon 20 insertion mutation comprises one or more insertions of 3-18 nucleotides between amino acids 770-785. Exemplary EGFR and HER exon 20 insertion mutations are depicted in FIG. 1 of the present disclosure.

"Hybridize" or "hybridization" refers to the binding between nucleic acids. The conditions for hybridization can be varied according to the sequence homology of the nucleic acids to be bound. Thus, if the sequence homology between the subject nucleic acids is high, stringent conditions are used. If the sequence homology is low, mild conditions are used. When the hybridization conditions are stringent, the hybridization specificity increases, and this increase of the hybridization specificity leads to a decrease in the yield of non-specific hybridization products. However, under mild hybridization conditions, the hybridization specificity decreases, and this decrease in the hybridization specificity leads to an increase in the yield of non-specific hybridization products.

A "probe" or "probes" refers to a polynucleotide that is at least eight (8) nucleotides in length and which forms a hybrid structure with a target sequence, due to complementarity of at least one sequence in the probe with a sequence in the target region. The polynucleotide can be composed of DNA and/or RNA. Probes in certain embodiments, are detectably labeled. Probes can vary significantly in size. Generally, probes are, for example, at least 8 to 15 nucleotides in length. Other probes are, for example, at least 20, 30 or 40 nucleotides long. Still other probes are somewhat longer, being at least, for example, 50, 60, 70, 80, or 90 nucleotides long. Probes can be of any specific length that falls within the foregoing ranges as well. Preferably, the probe does not contain a sequence complementary to the sequence(s) used to prime for a target sequence during the polymerase chain reaction.

"Oligonucleotide" or "polynucleotide" refers to a polymer of a single-stranded or double-stranded deoxyribonucleotide or ribonucleotide, which may be unmodified RNA or DNA or modified RNA or DNA.

A "modified ribonucleotide" or deoxyribonucleotide refer to molecules that can be used in place of naturally occurring bases in nucleic acid and includes, but is not limited to, modified purines and pyrimidines, minor bases, convertible nucleosides, structural analogs of purines and pyrimidines, labeled, derivatized and modified nucleosides and nucleotides, conjugated nucleosides and nucleotides, sequence modifiers, terminus modifiers, spacer modifiers, and nucleotides with backbone modifications, including, but not limited to, ribose-modified nucleotides, phosphoramidates, phosphorothioates, phosphonamidites, methyl phosphonates, methyl phosphoramidites, methyl phosphonamidites, 5'-β-cyanoethyl phosphoramidites, methylenephosphonates, phosphorodithioates, peptide nucleic acids, achiral and neutral internucleotidic linkages.

A "variant" refers to a polynucleotide or polypeptide that differs relative to a wild-type or the most prevalent form in a population of individuals by the exchange, deletion, or insertion of one or more nucleotides or amino acids, respectively. The number of nucleotides or amino acids exchanged, deleted, or inserted can be 1, 2, 3, 4, 5, 6, 7, 8, 9, 10, 11, 12, 13, 14, 15, 16, 17, 18, 19, 20 or more such as 25, 30, 35, 40, 45 or 50.

A "primer" or "primer sequence" refers to an oligonucleotide that hybridizes to a target nucleic acid sequence (for example, a DNA template to be amplified) to prime a nucleic acid synthesis reaction. The primer may be a DNA oligonucleotide, a RNA oligonucleotide, or a chimeric sequence. The primer may contain natural, synthetic, or modified nucleotides. Both the upper and lower limits of the length of the primer are empirically determined. The lower limit on primer length is the minimum length that is required to form a stable duplex upon hybridization with the target nucleic acid under nucleic acid amplification reaction conditions. Very short primers (usually less than 3-4 nucleotides long) do not form thermodynamically stable duplexes with target nucleic acid under such hybridization conditions. The upper limit is often determined by the possibility of having a duplex formation in a region other than the pre-determined nucleic acid sequence in the target nucleic acid. Generally, suitable primer lengths are in the range of about 10 to about 40 nucleotides long. In certain embodiments, for example, a primer can be 10-40, 15-30, or 10-20 nucleotides long. A primer is capable of acting as a point of initiation of synthesis on a polynucleotide sequence when placed under appropriate conditions.

"Detection," "detectable" and grammatical equivalents thereof refers to ways of determining the presence and/or quantity and/or identity of a target nucleic acid sequence. In some embodiments, detection occurs amplifying the target nucleic acid sequence. In other embodiments, sequencing of the target nucleic acid can be characterized as "detecting" the target nucleic acid. A label attached to the probe can include any of a variety of different labels known in the art that can be detected by, for example, chemical or physical means. Labels that can be attached to probes may include, for example, fluorescent and luminescence materials.

"Amplifying," "amplification," and grammatical equivalents thereof refers to any method by which at least a part of a target nucleic acid sequence is reproduced in a template-dependent manner, including without limitation, a broad range of techniques for amplifying nucleic acid sequences, either linearly or exponentially. Exemplary means for performing an amplifying step include ligase chain reaction (LCR), ligase detection reaction (LDR), ligation followed by Q-replicase amplification, PCR, primer extension, strand displacement amplification (SDA), hyperbranched strand displacement amplification, multiple displacement amplification (MDA), nucleic acid strand-based amplification (NASBA), two-step multiplexed amplifications, rolling circle amplification (RCA), recombinase-polymerase amplification (RPA) (TwistDx, Cambridg, UK), and self-sustained sequence replication (3SR), including multiplex versions or combinations thereof, for example but not limited to, OLA/PCR, PCR/OLA, LDR/PCR, PCR/PCR/LDR, PCR/LDR, LCR/PCR, PCR/LCR (also known as combined chain reaction-CCR), and the like. Descriptions of such techniques can be found in, among other places, Sambrook et al. Molecular Cloning, $3^{rd}$ Edition).

"EGFR" or "Epidermal growth factor receptor" or "EGFR" refers to a tyrosine kinase cell surface receptor and is encoded by one of four alternative transcripts appearing as GenBank accession NM_005228.3, NM_201282.1, NM_201283.1 and NM_201284.1. Variants of EGFR include an insertion in exon 20.

"HER2" or "ERBB2" is a member of the EGFR/ErbB family and appears as GenBank accession NM_004448.2. Variants of HER2 include an insertion in exon 20.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds of the present invention which are pharmaceutically acceptable, as defined above, and which possess the desired pharmacological activity. Non-limiting examples of such salts include acid addition salts formed with inorganic acids such as hydrochloric acid, hydrobromic acid, sulfuric acid, nitric acid, and phosphoric acid; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, and trimethylacetic acid. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Non-limiting examples of acceptable organic bases include ethanolamine, diethanolamine, triethanolamine, tromethamine, and N-methylglucamine. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

II. EGFR AND HER2 EXON 20 MUTATIONS

Certain embodiments of the present disclosure concern determining if a subject has one or more EGFR and/or HER2 exon 20 mutations, such as an insertion mutations, particularly one or more insertion mutations as depicted in FIG. 1. The subject may have 2, 3, 4, or more EGFR exon 20 mutations and/or HER2 exon 20 mutations. Mutation detection methods are known the art including PCR analyses and nucleic acid sequencing as well as FISH and CGH. In particular aspects, the exon 20 mutations are detected by DNA sequencing, such as from a tumor or circulating free DNA from plasma.

The EGFR exon 20 mutation(s) may comprise one or more point mutations, insertions, and/or deletions of 3-18 nucleotides between amino acids 763-778. The one or more EGFR exon 20 mutations may be located at one or more residues selected from the group consisting of A763, A767, S768, V769, D770, N771, P772, and H773.

EGFR exon 20 insertions may include H773_V774insH, A767_v769ASV, N771_P772insH, D770_N771insG, H779_V774insH, N771delinsHH, S768_D770dupDVD, A767_V769dupASV, A767_V769dupASV, P772_H773-dup, N771_H773dupNPH, S768_D770dupSVD, N771delinsGY, S768_D770delinsSVD, D770_D770delinsGY, A767_V769dupASV, and/or H773dup. In particular aspects, the exon 20 mutations are A763insFQEA, A767insASV, S768dupSVD, V769insASV, D770insSVD, D770insNPG, H773insNPH, N771del insGY, N771del insFH and/or N771dupNPH.

In some aspects, the subject may have or develop a mutation at EGFR residue C797 which may result in resistance to the TKI, such as poziotinib. Thus, in certain aspects, the subject is determined to not have a mutation at EGFR C797.

The HER2 exon 20 mutation may comprise one or more point mutations, insertions, and/or deletions of 3-18 nucleotides between amino acids 770-785. The one or more HER2 exon 20 mutations may be at residue A775, G776, S779, and/or P780. The one or more HER2 exon 20 mutations may be A775insV G776C, A775insYVMA, G776V, G776C V777insV, G776C V777insC, G776del insVV, G776del insVC, and/or P780insGSP.

The patient sample can be any bodily tissue or fluid that includes nucleic acids from the lung cancer in the subject. In certain embodiments, the sample will be a blood sample comprising circulating tumor cells or cell free DNA. In other embodiments, the sample can be a tissue, such as a lung tissue. The lung tissue can be from a tumor tissue and may be fresh frozen or formalin-fixed, paraffin-embedded (FFPE). In certain embodiments, a lung tumor FFPE sample is obtained.

Samples that are suitable for use in the methods described herein contain genetic material, e.g., genomic DNA (gDNA). Genomic DNA is typically extracted from biological samples such as blood or mucosal scrapings of the lining of the mouth, but can be extracted from other biological samples including urine, tumor, or expectorant. The sample itself will typically include nucleated cells (e.g., blood or buccal cells) or tissue removed from the subject including normal or tumor tissue. Methods and reagents are known in the art for obtaining, processing, and analyzing samples. In some embodiments, the sample is obtained with the assistance of a health care provider, e.g., to draw blood. In some embodiments, the sample is obtained without the assistance of a health care provider, e.g., where the sample is obtained non-invasively, such as a sample comprising buccal cells that is obtained using a buccal swab or brush, or a mouthwash sample.

In some cases, a biological sample may be processed for DNA isolation. For example, DNA in a cell or tissue sample can be separated from other components of the sample. Cells can be harvested from a biological sample using standard techniques known in the art. For example, cells can be harvested by centrifuging a cell sample and resuspending the pelleted cells. The cells can be resuspended in a buffered solution such as phosphate-buffered saline (PBS). After centrifuging the cell suspension to obtain a cell pellet, the cells can be lysed to extract DNA, e.g., gDNA. See, e.g., Ausubel et al. (2003). The sample can be concentrated and/or purified to isolate DNA. All samples obtained from a subject, including those subjected to any sort of further processing, are considered to be obtained from the subject. Routine methods can be used to extract genomic DNA from a biological sample, including, for example, phenol extraction. Alternatively, genomic DNA can be extracted with kits such as the QIAamp® Tissue Kit (Qiagen, Chatsworth, Calif.) and the Wizard® Genomic DNA purification kit (Promega). Non-limiting examples of sources of samples include urine, blood, and tissue.

The presence or absence of EGFR or HER2 exon 20 mutations, such as an exon 20 insertion mutation, as described herein can be determined using methods known in the art. For example, gel electrophoresis, capillary electrophoresis, size exclusion chromatography, sequencing, and/or arrays can be used to detect the presence or absence of insertion mutations. Amplification of nucleic acids, where desirable, can be accomplished using methods known in the art, e.g., PCR. In one example, a sample (e.g., a sample comprising genomic DNA), is obtained from a subject. The DNA in the sample is then examined to determine the identity of an insertion mutation as described herein. An insertion mutation can be detected by any method described herein, e.g., by sequencing or by hybridization of the gene in the genomic DNA, RNA, or cDNA to a nucleic acid probe, e.g., a DNA probe (which includes cDNA and oligonucleotide probes) or an RNA probe. The nucleic acid probe can be designed to specifically or preferentially hybridize with a particular variant.

A set of probes typically refers to a set of primers, usually primer pairs, and/or detectably-labeled probes that are used to detect the target genetic variations (e.g., EGFR and/or HER2 exon 20 mutations) used in the actionable treatment recommendations of the present disclosure. The primer pairs are used in an amplification reaction to define an amplicon that spans a region for a target genetic variation for each of the aforementioned genes. The set of amplicons are detected by a set of matched probes. In an exemplary embodiment, the present methods may use TaqMan™ (Roche Molecular Systems, Pleasanton, Calif.) assays that are used to detect a set of target genetic variations, such as EGFR and/or HER2 exon 20 mutations. In one embodiment, the set of probes are a set of primers used to generate amplicons that are detected by a nucleic acid sequencing reaction, such as a next generation sequencing reaction. In these embodiments, for example, AmpliSEQ™ (Life Technologies/Ion Torrent, Carlsbad, Calif.) or TruSEQ™ (Illumina, San Diego, Calif.) technology can be employed.

Analysis of nucleic acid markers can be performed using techniques known in the art including, without limitation, sequence analysis, and electrophoretic analysis. Non-limiting examples of sequence analysis include Maxam-Gilbert sequencing, Sanger sequencing, capillary array DNA sequencing, thermal cycle sequencing (Sears et al., 1992), solid-phase sequencing (Zimmerman et al., 1992), sequencing with mass spectrometry such as matrix-assisted laser desorption/ionization time-of-flight mass spectrometry (MALDI-TOF/MS; Fu et al., 1998), and sequencing by hybridization (Chee et al., 1996; Drmanac et al., 1993; Drmanac et al., 1998). Non-limiting examples of electrophoretic analysis include slab gel electrophoresis such as agarose or polyacrylamide gel electrophoresis, capillary electrophoresis, and denaturing gradient gel electrophoresis. Additionally, next generation sequencing methods can be performed using commercially available kits and instruments from companies such as the Life Technologies/Ion Torrent PGM or Proton, the Illumina HiSEQ or MiSEQ, and the Roche/454 next generation sequencing system.

Other methods of nucleic acid analysis can include direct manual sequencing (Church and Gilbert, 1988; Sanger et al., 1977; U.S. Pat. No. 5,288,644); automated fluorescent sequencing; single-stranded conformation polymorphism assays (SSCP) (Schafer et al., 1995); clamped denaturing gel electrophoresis (CDGE); two-dimensional gel electrophoresis (2DGE or TDGE); conformational sensitive gel electrophoresis (CSGE); denaturing gradient gel electrophoresis (DGGE) (Sheffield et al., 1989); denaturing high performance liquid chromatography (DHPLC, Underhill et al., 1997); infrared matrix-assisted laser desorption/ionization (IR-MALDI) mass spectrometry (WO 99/57318); mobility shift analysis (Orita et al., 1989); restriction enzyme analysis (Flavell et al., 1978; Geever et al., 1981); quantitative real-time PCR (Raca et al., 2004); heteroduplex analysis; chemical mismatch cleavage (CMC) (Cotton et al., 1985); RNase protection assays (Myers et al., 1985); use of polypeptides that recognize nucleotide mismatches, e.g., *E. coli* mutS protein; allele-specific PCR, and combinations of such methods. See, e.g., U.S. Patent Publication No. 2004/0014095, which is incorporated herein by reference in its entirety.

In one example, a method of identifying an EGFR and/or HER2 mutation in a sample comprises contacting a nucleic acid from said sample with a nucleic acid probe that is capable of specifically hybridizing to nucleic acid encoding a mutated EGFR or HER2 protein, or fragment thereof incorporating a mutation, and detecting said hybridization. In a particular embodiment, said probe is detectably labeled such as with a radioisotope ($^3$H, $^{32}$P, or $^{33}$P), a fluorescent agent (rhodamine, or fluorescein) or a chromogenic agent. In a particular embodiment, the probe is an antisense oligomer, for example PNA, morpholino-phosphoramidates, LNA or 2'-alkoxyalkoxy. The probe may be from about 8 nucleotides to about 100 nucleotides, or about 10 to about 75, or about 15 to about 50, or about 20 to about 30. In another aspect, said probes of the present disclosure are provided in a kit for identifying EGFR or HER2 mutations in a sample, said kit comprising an oligonucleotide that specifically hybridizes to or adjacent to a site of mutation in the EGFR or HER2 gene. The kit may further comprise instructions for treating patients having tumors that contain EGFR or HER2 insertion mutations with poziotinib or afatinib based on the result of a hybridization test using the kit.

In another aspect, a method for detecting an exon 20 mutation in a sample comprises amplifying from said sample nucleic acids corresponding to exon 20 of said EGFR gene or HER2, or a fragment thereof suspected of containing a mutation, and comparing the electrophoretic mobility of the amplified nucleic acid to the electrophoretic mobility of corresponding wild-type EGFR or HER2 gene or fragment thereof. A difference in the mobility indicates the presence of a mutation in the amplified nucleic acid sequence. Electrophoretic mobility may be determined on polyacrylamide gel.

Alternatively, nucleic acids may be analyzed for detection of mutations using Enzymatic Mutation Detection (EMD) (Del Tito et al., 1998). EMD uses the bacteriophage resolvase T4 endonuclease VII, which scans along double-stranded DNA until it detects and cleaves structural distortions caused by base pair mismatches resulting from point mutations, insertions and deletions. Detection of two short fragments formed by resolvase cleavage, for example by gel electrophoresis, indicates the presence of a mutation. Benefits of the EMD method are a single protocol to identify point mutations, deletions, and insertions assayed directly from PCR reactions eliminating the need for sample purification, shortening the hybridization time, and increasing the signal-to-noise ratio. Mixed samples containing up to a 20-fold excess of normal DNA and fragments up to 4 kb in size can been assayed. However, EMD scanning does not identify particular base changes that occur in mutation positive samples requiring additional sequencing procedures to identity of the mutation if necessary. CEL I enzyme can be used similarly to resolvase T4 endonuclease VII as demonstrated in U.S. Pat. No. 5,869,245.

III. METHODS OF TREATMENT

Further provided herein are methods for treating or delaying progression of cancer in an individual comprising administering to the individual an effective amount of poziotinib, afatinib, or a structurally similar inhibitor, to a subject determined to have an EGFR and/or HER2 exon 20 mutations, such as an exon 20 insertion. The subject may have more than one EGFR and/or HER exon 20 mutation.

Examples of cancers contemplated for treatment include lung cancer, head and neck cancer, breast cancer, pancreatic cancer, prostate cancer, renal cancer, bone cancer, testicular cancer, cervical cancer, gastrointestinal cancer, lymphomas, pre-neoplastic lesions in the lung, colon cancer, melanoma, and bladder cancer. In particular aspects, the cancer is non-small cell lung cancer.

In some embodiments, the subject is a mammal, e.g., a primate, preferably a higher primate, e.g., a human (e.g., a patient having, or at risk of having, a disorder described herein). In one embodiment, the subject is in need of enhancing an immune response. In certain embodiments, the subject is, or is at risk of being, immunocompromised. For example, the subject is undergoing or has undergone a chemotherapeutic treatment and/or radiation therapy. Alternatively, or in combination, the subject is, or is at risk of being, immunocompromised as a result of an infection.

Certain embodiments concern the administration of poziotinib (also known as HM781-36B, HM781-36, and 1-[4-[4-(3,4-dichloro-2-fluoroanilino)-7-methoxyquinazolin-6-yl]oxypiperidin-1-yl]prop-2-en-1-one) to a subject determined to have EGFR or HER2 exon 20 mutation, such as an exon 20 insertion. Poziotinib is a quinazoline-based pan-HER inhibitor that irreversibly blocks signaling through the HER family of tyrosine-kinase receptors including HER1, HER2, and HER4. Poziotinib or structurally similar compounds (e.g., U.S. Pat. No. 8,188,102 and U.S. Patent Publication No. 20130071452; incorporated herein by reference) may be used in the present methods.

B. Pharmaceutical Compositions

Also provided herein are pharmaceutical compositions and formulations comprising poziotinib or afatinib and a pharmaceutically acceptable carrier for subjects determined to have an EGFR or HER2 exon 20 mutation, such as an exon 20 insertion.

Pharmaceutical compositions and formulations as described herein can be prepared by mixing the active ingredients (such as an antibody or a polypeptide) having the desired degree of purity with one or more optional pharmaceutically acceptable carriers (Remington's Pharmaceutical Sciences 22$^{nd}$ edition, 2012), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in U.S. Patent Publication Nos. 2005/0260186 and 2006/0104968. In one aspect, a sHASEGP is combined with one or more additional glycosaminoglycanases such as chondroitinases.

C. Combination Therapies

In certain embodiments, the compositions and methods of the present embodiments involve poziotinib or afatinib in combination with at least one additional therapy. The additional therapy may be radiation therapy, surgery (e.g., lumpectomy and a mastectomy), chemotherapy, gene therapy, DNA therapy, viral therapy, RNA therapy, immunotherapy, bone marrow transplantation, nanotherapy, monoclonal antibody therapy, or a combination of the foregoing. The additional therapy may be in the form of adjuvant or neoadjuvant therapy.

In some embodiments, the additional therapy is the administration of small molecule enzymatic inhibitor or anti-metastatic agent. In some embodiments, the additional therapy is the administration of side-effect limiting agents (e.g., agents intended to lessen the occurrence and/or severity of side effects of treatment, such as anti-nausea agents, etc.). In some embodiments, the additional therapy is radiation therapy. In some embodiments, the additional therapy is surgery. In some embodiments, the additional therapy is a combination of radiation therapy and surgery. In some embodiments, the additional therapy is gamma irradiation. In some embodiments, the additional therapy is therapy targeting PBK/AKT/mTOR pathway, HSP90 inhibitor, tubulin inhibitor, apoptosis inhibitor, and/or chemopreventative agent. The additional therapy may be one or more of the chemotherapeutic agents known in the art.

The poziotinib or afatinib may be administered before, during, after, or in various combinations relative to an additional cancer therapy, such as immune checkpoint therapy. The administrations may be in intervals ranging from concurrently to minutes to days to weeks. In embodiments where the poziotinib or afatinib is provided to a patient separately from an additional therapeutic agent, one would generally ensure that a significant period of time did not expire between the time of each delivery, such that the two compounds would still be able to exert an advantageously combined effect on the patient. In such instances, it is contemplated that one may provide a patient with the antibody therapy and the anti-cancer therapy within about 12 to 24 or 72 h of each other and, more particularly, within about 6-12 h of each other. In some situations it may be desirable to extend the time period for treatment significantly where several days (2, 3, 4, 5, 6, or 7) to several weeks (1, 2, 3, 4, 5, 6, 7, or 8) lapse between respective administrations.

Various combinations may be employed. For the example below poziotinib or afatinib is "A" and an anti-cancer therapy is "B":

A/B/A B/A/B B/B/A A/A/B A/B/B B/A/A A/B/B/B B/A/B/B
B/B/B/A B/B/A/B A/A/B/B A/B/A/B A/B/B/A B/B/A/A
B/A/B/A B/A/A/B A/A/A/B B/A/A/A A/B/A/A A/A/B/A

Administration of any compound or therapy of the present embodiments to a patient will follow general protocols for the administration of such compounds, taking into account the toxicity, if any, of the agents. Therefore, in some embodiments there is a step of monitoring toxicity that is attributable to combination therapy.

1. Chemotherapy

A wide variety of chemotherapeutic agents may be used in accordance with the present embodiments. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammall and calicheamicin omegall); dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids, such as retinoic acid; capecitabine; carboplatin, procarbazine, plicomycin, gemcitabien, navelbine, farnesyl-protein transferase inhibitors, transplatinum, and pharmaceutically acceptable salts, acids, or derivatives of any of the above.

2. Radiotherapy

Other factors that cause DNA damage and have been used extensively include what are commonly known as γ-rays, X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287), and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

3. Immunotherapy

The skilled artisan will understand that additional immunotherapies may be used in combination or in conjunction with methods of the embodiments. In the context of cancer treatment, immunotherapeutics, generally, rely on the use of immune effector cells and molecules to target and destroy cancer cells. Rituximab (RITUXAN®) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve as a targeting agent. Alternatively, the effector may be a lymphocyte carrying a surface molecule that interacts, either directly or indirectly, with a tumor cell target. Various effector cells include cytotoxic T cells and NK cells Antibody-drug conjugates have emerged as a breakthrough approach to the development of cancer therapeutics. Cancer is one of the leading causes of deaths in the world. Antibody-drug conjugates (ADCs) comprise monoclonal antibodies (MAbs) that are covalently linked to cell-killing drugs. This approach combines the high specificity of MAbs against their antigen targets with highly potent cytotoxic drugs, resulting in "armed" MAbs that deliver the payload (drug) to tumor cells with enriched levels of the antigen. Targeted delivery of the drug also minimizes its exposure in normal tissues, resulting in decreased toxicity and improved therapeutic index. The approval of two ADC drugs, ADCETRIS® (brentuximab vedotin) in 2011 and KADCYLA® (trastuzumab emtansine or T-DM1) in 2013 by FDA validated the approach. There are currently more than 30 ADC drug candidates in various stages of clinical trials for cancer treatment (Leal et al., 2014). As antibody engineering and linker-payload optimization are becoming more and more mature, the discovery and development of new ADCs are increasingly dependent on the identification and validation of new targets that are suitable to this approach and the generation of targeting MAbs. Two criteria for ADC targets are upregulated/high levels of expression in tumor cells and robust internalization.

In one aspect of immunotherapy, the tumor cell must bear some marker that is amenable to targeting, i.e., is not present on the majority of other cells. Many tumor markers exist and any of these may be suitable for targeting in the context of the present embodiments. Common tumor markers include CD20, carcinoembryonic antigen, tyrosinase (p97), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

Examples of immunotherapies include immune adjuvants, e.g., *Mycobacterium bovis, Plasmodium falciparum*, dinitrochlorobenzene, and aromatic compounds (U.S. Pat. Nos. 5,801,005 and 5,739,169; Hui and Hashimoto, 1998; Christodoulides et al., 1998); cytokine therapy, e.g., interferons α, β, and γ, IL-1, GM-CSF, and TNF (Bukowski et al., 1998; Davidson et al., 1998; Hellstrand et al., 1998); gene therapy, e.g., TNF, IL-1, IL-2, and p53 (Qin et al., 1998; Austin-Ward and Villaseca, 1998; U.S. Pat. Nos. 5,830,880 and 5,846,945); and monoclonal antibodies, e.g., anti-CD20, anti-ganglioside GM2, and anti-p185 (Hollander, 2012; Hanibuchi et al., 1998; U.S. Pat. No. 5,824,311). It is contemplated that one or more anti-cancer therapies may be employed with the antibody therapies described herein.

In some embodiments, the immunotherapy may be an immune checkpoint inhibitor. Immune checkpoints either turn up a signal (e.g., co-stimulatory molecules) or turn down a signal. Inhibitory immune checkpoints that may be targeted by immune checkpoint blockade include adenosine A2A receptor (A2AR), B7-H3 (also known as CD276), B and T lymphocyte attenuator (BTLA), cytotoxic T-lymphocyte-associated protein 4 (CTLA-4, also known as CD152), indoleamine 2,3-dioxygenase (IDO), killer-cell immunoglobulin (KIR), lymphocyte activation gene-3 (LAGS), programmed death 1 (PD-1), T-cell immunoglobulin domain and mucin domain 3 (TIM-3) and V-domain Ig suppressor of T cell activation (VISTA). In particular, the immune checkpoint inhibitors target the PD-1 axis and/or CTLA-4.

The immune checkpoint inhibitors may be drugs such as small molecules, recombinant forms of ligand or receptors, or, in particular, are antibodies, such as human antibodies (e.g., International Patent Publication WO2015016718; Pardoll, *Nat Rev Cancer*, 12(4): 252-64, 2012; both incorporated herein by reference). Known inhibitors of the immune checkpoint proteins or analogs thereof may be used, in particular chimerized, humanized or human forms of antibodies may be used. As the skilled person will know, alternative and/or equivalent names may be in use for certain antibodies mentioned in the present disclosure. Such alternative and/or equivalent names are interchangeable in the context of the present invention. For example it is known that lambrolizumab is also known under the alternative and equivalent names MK-3475 and pembrolizumab.

In some embodiments, the PD-1 binding antagonist is a molecule that inhibits the binding of PD-1 to its ligand binding partners. In a specific aspect, the PD-1 ligand binding partners are PDL1 and/or PDL2. In another embodiment, a PDL1 binding antagonist is a molecule that inhibits the binding of PDL1 to its binding partners. In a specific aspect, PDL1 binding partners are PD-1 and/or B7-1. In another embodiment, the PDL2 binding antagonist is a molecule that inhibits the binding of PDL2 to its binding partners. In a specific aspect, a PDL2 binding partner is PD-1. The antagonist may be an antibody, an antigen binding fragment thereof, an immunoadhesin, a fusion protein, or oligopeptide. Exemplary antibodies are described in U.S. Pat. Nos. 8,735,553, 8,354,509, and 8,008,449, all incorporated herein by reference. Other PD-1 axis antagonists for use in the methods provided herein are known in the art such as described in U.S. Patent Publication Nos. US20140294898, US2014022021, and US20110008369, all incorporated herein by reference.

In some embodiments, the PD-1 binding antagonist is an anti-PD-1 antibody (e.g., a human antibody, a humanized antibody, or a chimeric antibody). In some embodiments, the anti-PD-1 antibody is selected from the group consisting of nivolumab, pembrolizumab, and CT-011. In some embodiments, the PD-1 binding antagonist is an immunoadhesin (e.g., an immunoadhesin comprising an extracellular or PD-1 binding portion of PDL1 or PDL2 fused to a constant region (e.g., an Fc region of an immunoglobulin sequence). In some embodiments, the PD-1 binding antagonist is AMP-224. Nivolumab, also known as MDX-1106-04, MDX-1106, ONO-4538, BMS-936558, and OPDIVO®, is an anti-PD-1 antibody described in WO2006/121168. Pembrolizumab, also known as MK-3475, Merck 3475, lambrolizumab, KEYTRUDA®, and SCH-900475, is an anti-PD-1 antibody described in WO2009/114335. CT-011, also known as hBAT or hBAT-1, is an anti-PD-1 antibody described in WO2009/101611. AMP-224, also known as B7-DCIg, is a PDL2-Fc fusion soluble receptor described in WO2010/027827 and WO2011/066342.

Another immune checkpoint that can be targeted in the methods provided herein is the cytotoxic T-lymphocyte-associated protein 4 (CTLA-4), also known as CD152. The complete cDNA sequence of human CTLA-4 has the Genbank accession number L15006. CTLA-4 is found on the surface of T cells and acts as an "off" switch when bound to CD80 or CD86 on the surface of antigen-presenting cells. CTLA4 is a member of the immunoglobulin superfamily that is expressed on the surface of Helper T cells and transmits an inhibitory signal to T cells. CTLA4 is similar to the T-cell co-stimulatory protein, CD28, and both molecules bind to CD80 and CD86, also called B7-1 and B7-2 respectively, on antigen-presenting cells. CTLA4 transmits an inhibitory signal to T cells, whereas CD28 transmits a stimulatory signal. Intracellular CTLA4 is also found in regulatory T cells and may be important to their function. T cell activation through the T cell receptor and CD28 leads to increased expression of CTLA-4, an inhibitory receptor for B7 molecules.

In some embodiments, the immune checkpoint inhibitor is an anti-CTLA-4 antibody (e.g., a human antibody, a humanized antibody, or a chimeric antibody), an antigen binding fragment thereof, an immunoadhesin, a fusion protein, or oligopeptide.

Anti-human-CTLA-4 antibodies (or VH and/or VL domains derived therefrom) suitable for use in the present methods can be generated using methods well known in the art. Alternatively, art recognized anti-CTLA-4 antibodies can be used. For example, the anti-CTLA-4 antibodies disclosed in: U.S. Pat. No. 8,119,129; International Patent Publication Nos. WO 01/14424, WO 98/42752, and WO 00/37504 (CP675,206, also known as tremelimumab; formerly ticilimumab); U.S. Pat. No. 6,207,156; Hurwitz et al., 1998; Camacho et al., 2004; and Mokyr et al., 1998 can be used in the methods disclosed herein. The teachings of each of the aforementioned publications are hereby incorporated by reference. Antibodies that compete with any of these art-recognized antibodies for binding to CTLA-4 also can be used. For example, a humanized CTLA-4 antibody is described in International Patent Application Nos. WO2001014424, and WO2000037504, and U.S. Pat. No. 8,017,114; all incorporated herein by reference.

An exemplary anti-CTLA-4 antibody is ipilimumab (also known as 10D1, MDX-010, MDX-101, and Yervoy®) or antigen binding fragments and variants thereof (see, e.g., WO 01/14424). In other embodiments, the antibody comprises the heavy and light chain CDRs or VRs of ipilimumab. Accordingly, in one embodiment, the antibody comprises the CDR1, CDR2, and CDR3 domains of the VH region of ipilimumab, and the CDR1, CDR2 and CDR3 domains of the VL region of ipilimumab. In another embodiment, the antibody competes for binding with and/or binds to the same epitope on CTLA-4 as the above-mentioned antibodies. In another embodiment, the antibody has at least about 90% variable region amino acid sequence identity with the above-mentioned antibodies (e.g., at least about 90%, 95%, or 99% variable region identity with ipilimumab).

Other molecules for modulating CTLA-4 include CTLA-4 ligands and receptors such as described in U.S. Pat. Nos. 5,844,905, 5,885,796 and International Patent Application Nos. WO1995001994 and WO1998042752; all incorporated herein by reference, and immunoadhesins such as described in U.S. Pat. No. 8,329,867, incorporated herein by reference.

4. Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present embodiments, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

5. Other Agents

It is contemplated that other agents may be used in combination with certain aspects of the present embodiments to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions would increase the anti-hyperproliferative effects on the neighboring hyperproliferative cell population. In other embodiments, cytostatic or differentiation agents can be used in combination with certain aspects of the present embodiments to improve the anti-hyperproliferative efficacy of the treatments. Inhibitors of cell adhesion are contemplated to improve the efficacy of the present embodiments. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present embodiments to improve the treatment efficacy.

IV. KIT

Also within the scope of the present disclosure are kits for detecting EGFR and/or HER2 exon 20 mutations, such as those disclosed herein. An example of such a kit may include a set of exon 20 mutation-specific primer. The kit may further comprise instructions for use of the primers to detect the presence or absence of the specific EFGR and/or HER2 exon 20 mutations described herein. The kit may further comprise instructions for diagnostic purposes, indicating that a positive identification of EGFR and/or HER2 exon 20 mutations described herein in a sample from a cancer patient indicates sensitivity to the tyrosine kinase inhibitor poziotinib or afatinib or a structurally similar inhibitor. The kit may further comprise instructions that indicate that a positive identification of EGFR and/or exon 20 mutations described herein in a sample from a cancer patient indicates that a patient should be treated with poziotinib, afatinib, or a structurally similar inhibitor.

V. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Identification of Drugs for Cancer Cells with EGFR or HER Exon 20 Insertions

Figures 4A, 4B, 4C:
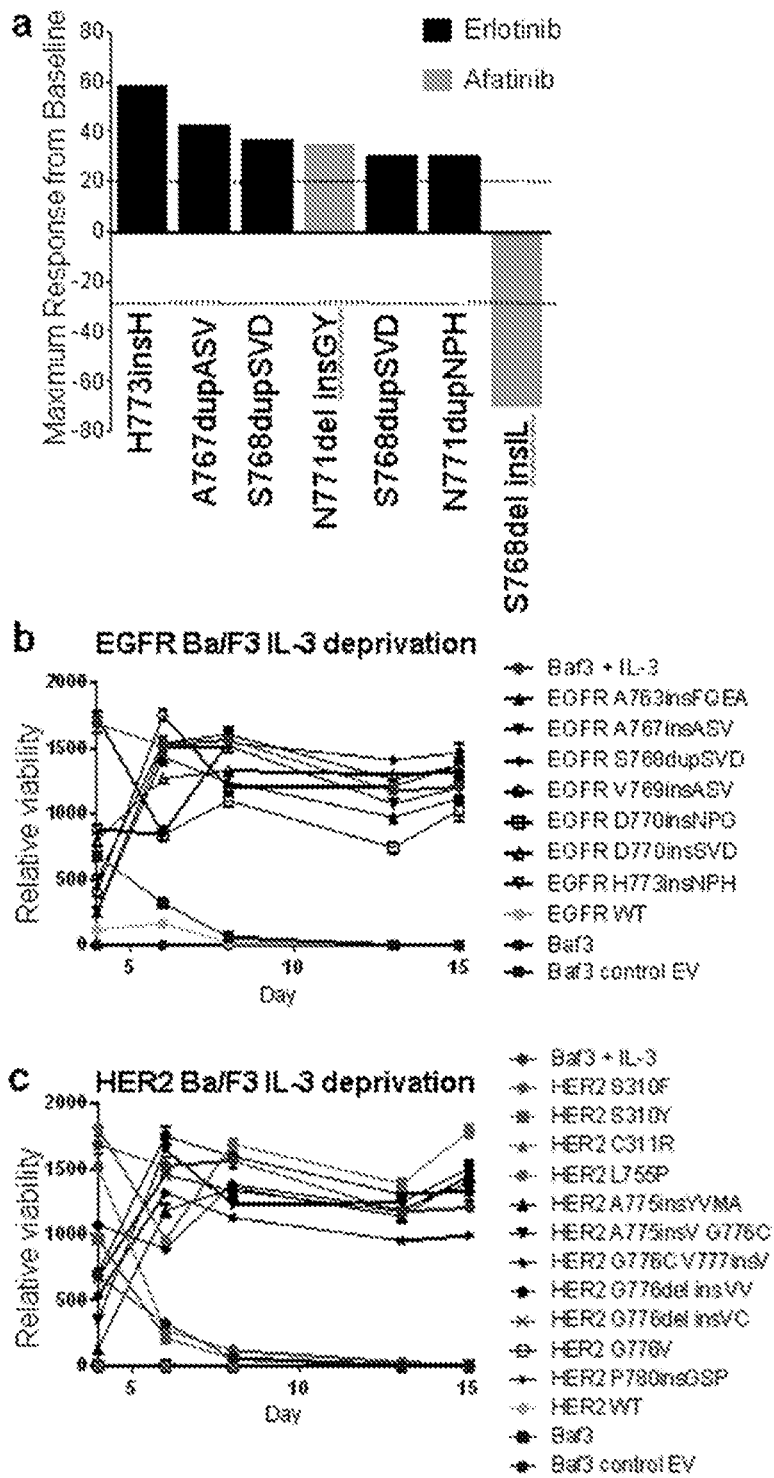
FIGS. 4A-4C: EGFR and HiER2 exon 20 insertion mutations are activating mutations.

Clinical responses to TKIs were investigated in patients with tumors harboring EGFR exon 20 insertions in the clinical database; and among 280 patients with EGFR mutant NSCLC, 129 patients were identified with classical EGFR mutations (exon 19 deletion, L858R, and L861Q) and 9 patients with EGFR exon 20 insertions that were treated with single agent erlotinib, gefitinib or afatinib. NSCLC patients with classical EGFR mutations had a median PFS of 14 months, whereas patients with EGFR exon 20 insertions had a median PFS of only 2 months (p<0.0001, log rank test; FIG. 1A). Of the 9 EGFR exon 20 insertion patients, OR was observed in only 1 patient harboring an S768del-insIL mutation who received afatinib (FIG. 4A). This clinical data demonstrates the limited activity of the available EGFR TKIs in EGFR exon 20 insertion driven NSCLC and validates that alternative treatment strategies are needed for these specific tumors.

Figure 5:
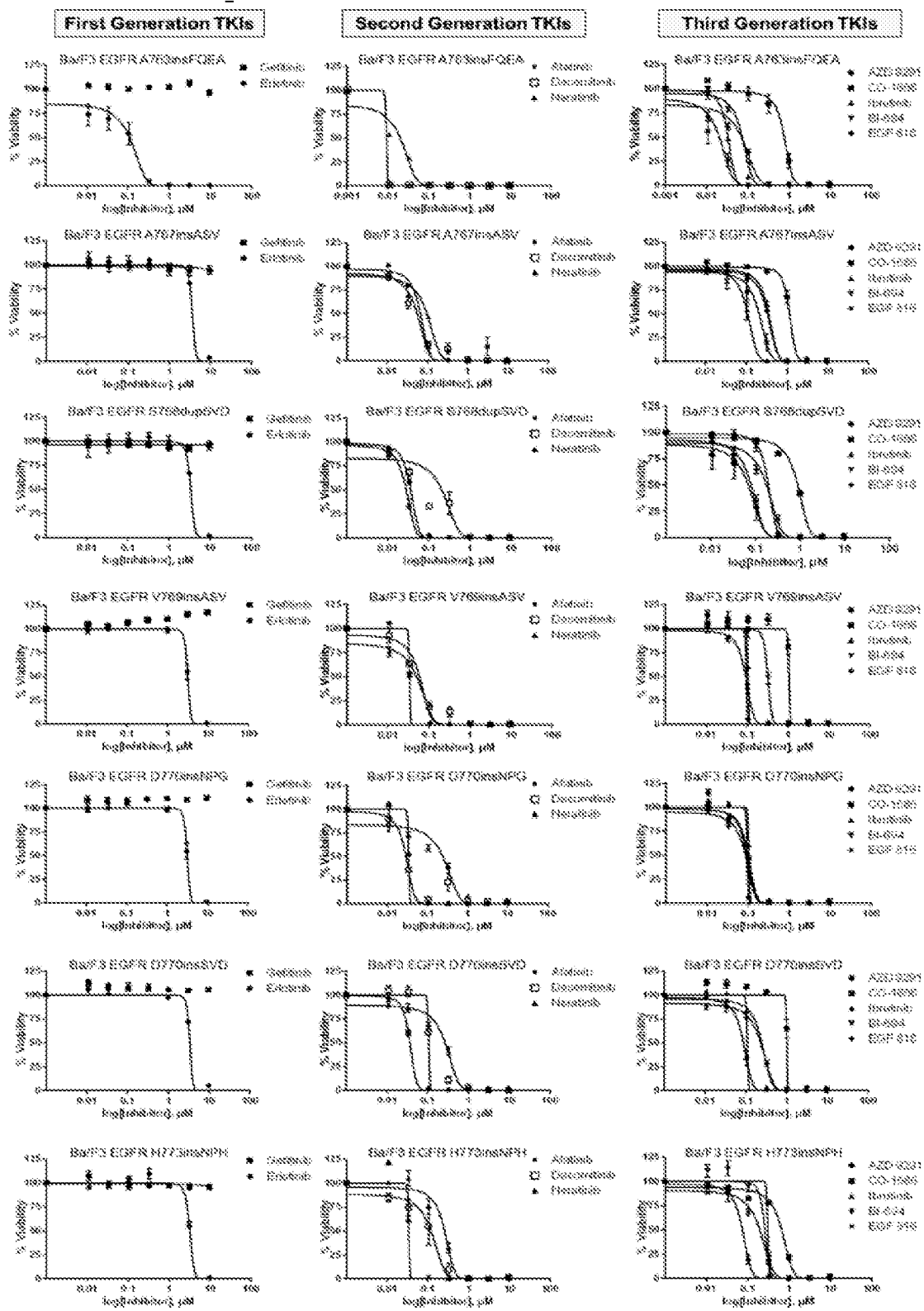
FIG. 5: Dose response curves of cell viability of individual Ba/F3 cell lines expressing EGFR exon 20 insertion mutations treated with 1st, 2nd, and 3rd generation TKIs for 72 hours. The mean±SEM is plotted for each concentration (n=3).
Figure 6:
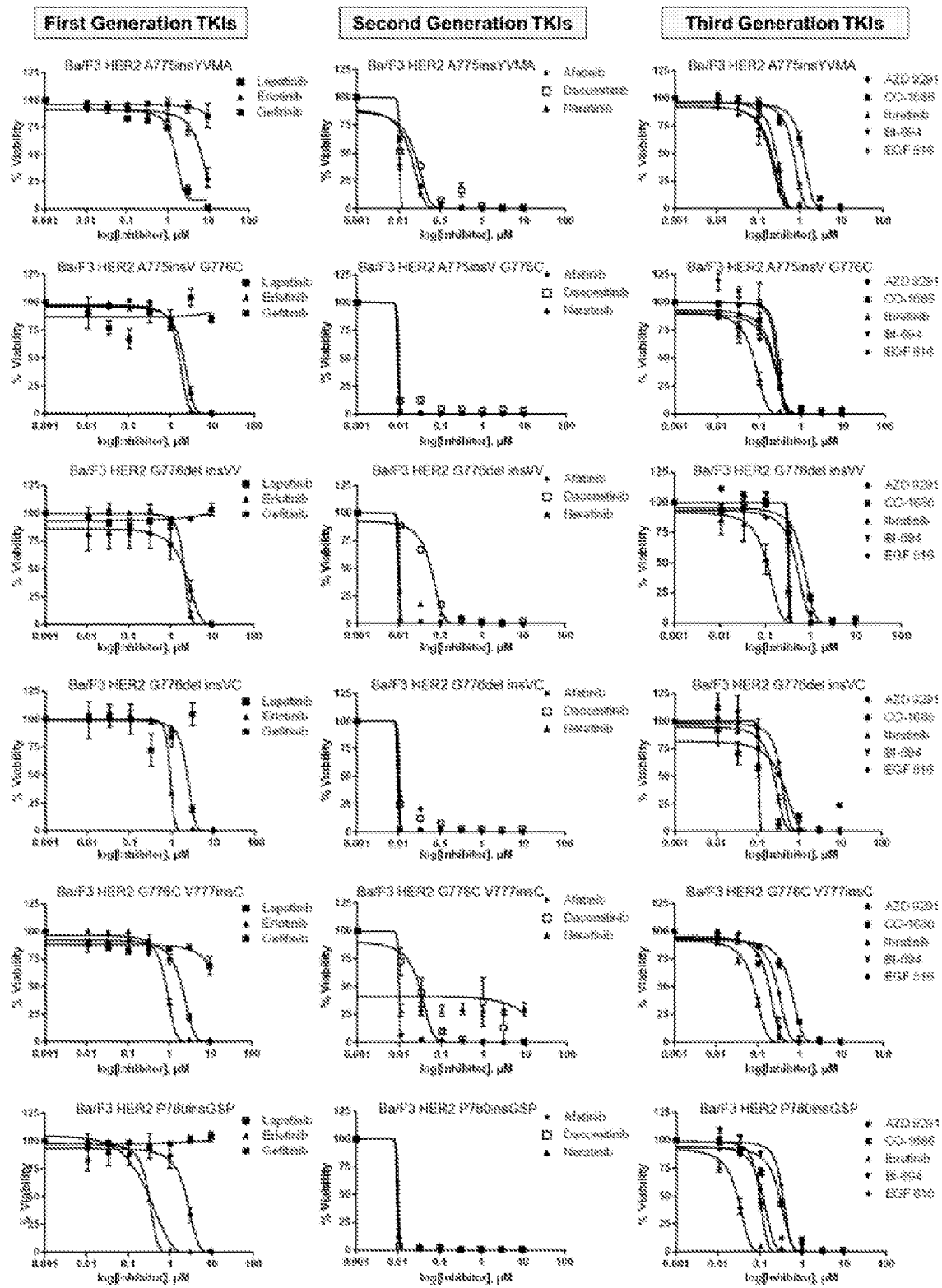
FIG. 6: Dose response curves of cell viability of individual Ba/F3 cell lines expressing HER2 exon 20 insertion mutations treated with 1st, 2nd, and 3rd generation TKIs for 72 hours. The mean±SEM is plotted for each concentration (n=3).
Figures 7A, 7B, 7C, 7D:
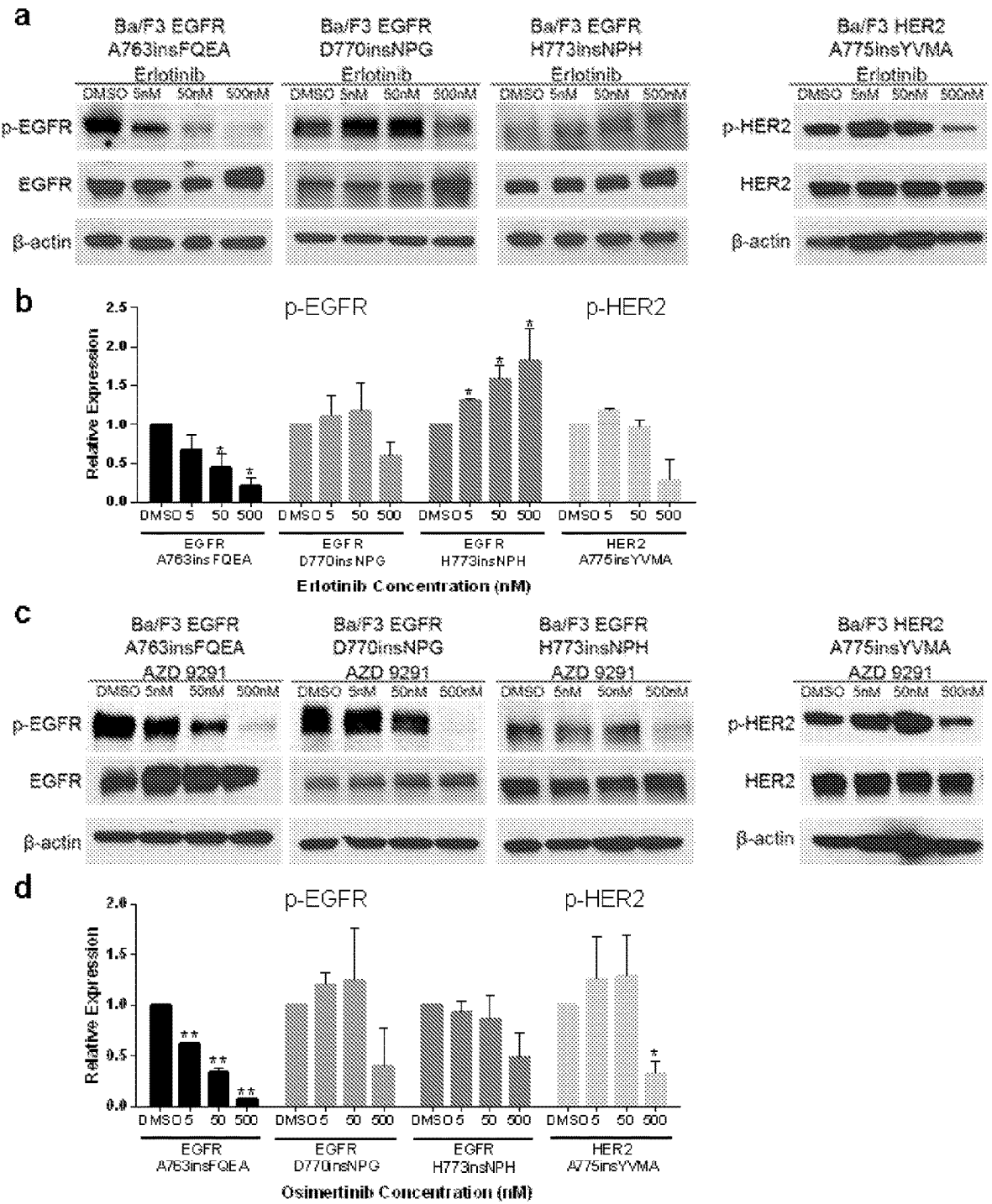
FIGS. 7A-7D: EGFR and HER2 exon 20 insertions mutations after residue A763 are resistant to 1st and 3rd generation TKIs. Ba/F3 cells with EGFR exon 20 insertions were serum starved for 1 hour then treated with indicated doses of (FIG. 7A) erlotinib or (FIG. 7C) osimertinib for 2 hours (N=2). p-EGFR and p-HER2 levels after (FIG. 7B) erlotinib treatment and (FIG. 7D) osimertinib treatment were quantified using Photoshop. Values were plotted in Graphpad Prism and bars are representative of mean±SEM. (N=2) p<0.05 (*), p<0.01 () or p<0.001 (*).

As an initial step in drug screening, 7 EGFR and 11 HER2 mutations were expressed in Ba/F3 cells. The locations of the EGFR and HER2 exon 20 mutations are summarized in FIG. 1B. To assess which exon 20 mutations of EGFR and HER2 are activating, Ba/F3 cell lines were screened for IL-3 independent survival. It was found that all EGFR exon 20 insertions tested were activating mutations (FIG. 4B), 6 HER2 exon 20 mutations and, L755P, located in exon 19, were activating mutations (FIG. 4C). Next, the sensitivity was tested for the exon 20 insertions to EGFR and HER2 TKIs that have undergone clinical evaluation including reversible (first generation), irreversible (second generation) and irreversible mutant-specific TKIs (third generation), and then compared sensitivity to EGFR L858R, a classical sensitizing mutation. With the exception of EGFR A763insFQEA, EGFR exon 20 insertions (n=6) were resistant to first (FIG. 1C, $IC_{50}$=3.3->10 μM), second (FIG. 1d, $IC_{50}$=40-135 nM), and third (FIG. 1e, $IC_{50}$=103-850 nM) generation EGFR TKIs (FIG. 5, Table 1). In addition, HER2 exon 20 mutants (n=6) were resistant to first (FIG. 1F, $IC_{50}$=1.2-13 μM) and third (FIG. 1H, $IC_{50}$=114-505 nM) generation TKIs. Second generation TKIs did have some activity against Ba/F3 HER2 exon 20 mutant cell lines (FIG. 1G, $IC_{50}$=10-12 nM, FIG. 6, Table 1). Consistent with the drug screening, with the exception of EGFR A763insFQEA, which showed partial inhibition at lower doses, western blotting demonstrated erlotinib and osimertinib did not significantly inhibit p-EGFR2 in EGFR exon 20 insertion mutations, and only significantly inhibited p-HER2 in HER2 exon 20 insertions mutants at 500 nM (FIG. 7A-D).

TABLE 1

IC50 values of EGFR and HER2 exon 20 insertions with EGFR/HER2 TKIs.

| | | Ave EGFR exon 20 insertions (N = 6 cell lines) | Ave HER2 exon 20 insertions (N = 6 cell lines) |
|---|---|---|---|
| 1st gen TKI | Erlotinib | 3,310 nM | 3,250 nM |
| | Gefitinib | >10,000 nM | 12,900 nM |
| | Lapatinib | — | 1,190 nM |
| | L858R + Erlotinib | 17.0 nM | |

TABLE 1-continued

IC50 values of EGFR and HER2 exon 20 insertions with EGFR/HER2 TKIs.

| | | Ave EGFR exon 20 insertions (N = 6 cell lines) | Ave HER2 exon 20 insertions (N = 6 cell lines) |
|---|---|---|---|
| 2nd gen TKI | Afatinib | 39.9 nM | 11.7 nM |
| | Dacomitinib | 61.1 nM | 12.4 nM |
| | Neratinib | 135 nM | 10.4 nM |
| | L858R + Afatinib | 0.876 nM | |
| 3rd gen TKI | Osimertinib | 103 nM | 444 nM |
| | Rociletinib | 850 nM | 505 nM |
| | Ibrutinib | 143 nM | 114 nM |
| | Olumtinib | 204 nM | 352 nM |
| | Nazartinib | 198 nM | 233 nM |
| | L858R/T790M + Osimertinib | 9.00 nM | |

To investigate why exon 20 insertions are resistant to first and third generation EGFR TKIs, 3-D modeling was performed on the solved crystal structures of EGFR D770insNPG with EGFR T790M and EGFR WT to visualize changes within the drug binding pocket. The modeling revealed that EGFR exon 20 insertions are similar to T790M mutations in the alignment of the gatekeeper residue T790, which results in increased affinity to ATP and a reduced binding of first generation inhibitors, rendering these mutations resistant to non-covalent inhibitors. In addition, HER2 exon 20 insertions induce a constitutively active conformation, preventing the binding of non-covalent HER2 inhibitor lapatinib, which binds to HER2 in the inactive conformation. Moreover, EGFR and HER2 exon 20 insertions have a dramatic effect on the drug binding pocket. In silico modeling of EGFR (FIG. 1I) and HER2 (FIG. 1J) exon 20 insertions revealed a significant shift of the α-c-helix into the drug binding pocket (arrow) due to the insertions at the C-terminal end of the α-c-helix (FIG. 1J), forcing a ridged placement of the α-c-helix in the inward, activated position. In addition, 3-D modeling demonstrated a significant shift of the P-loop into the drug binding pocket (FIGS. 1I, 1J) of both receptors. Together these shifts result in steric hindrance of the drug biding pocket from two directions in both EGFR and HER2 exon 20 mutant proteins. Consistent with the above mentioned in vitro testing, 3-D modeling supports the observation that afatinib inhibits exon 20 insertions more effectively than osimertinib. Osimertinib has a large terminal 1-methylindole group connected directly to a rigid pyrimidine core. This large inflexible group reduces the ability of osimertinib to reach the C797 residue as effectively as afatinib in EGFR exon 20 insertions (FIG. 1I). Alternatively, afatinib has a smaller 1-chloro-2-flurobenzene ring terminal group indirectly linked to a quinazoline core via a secondary amine group, enabling afatinib to fit into the sterically hindered binding pocket. Moreover, steric hindrance prevents binding of osimertinib to HER2 A775insYVMA. Taken together, the in vitro data and in silico modeling indicate that small, flexible quinazoline derivatives may be capable of targeting EGFR/HER2 exon 20 insertions.

Figures 2A, 2B, 2C, 2D, 2E, 2F, 2G:
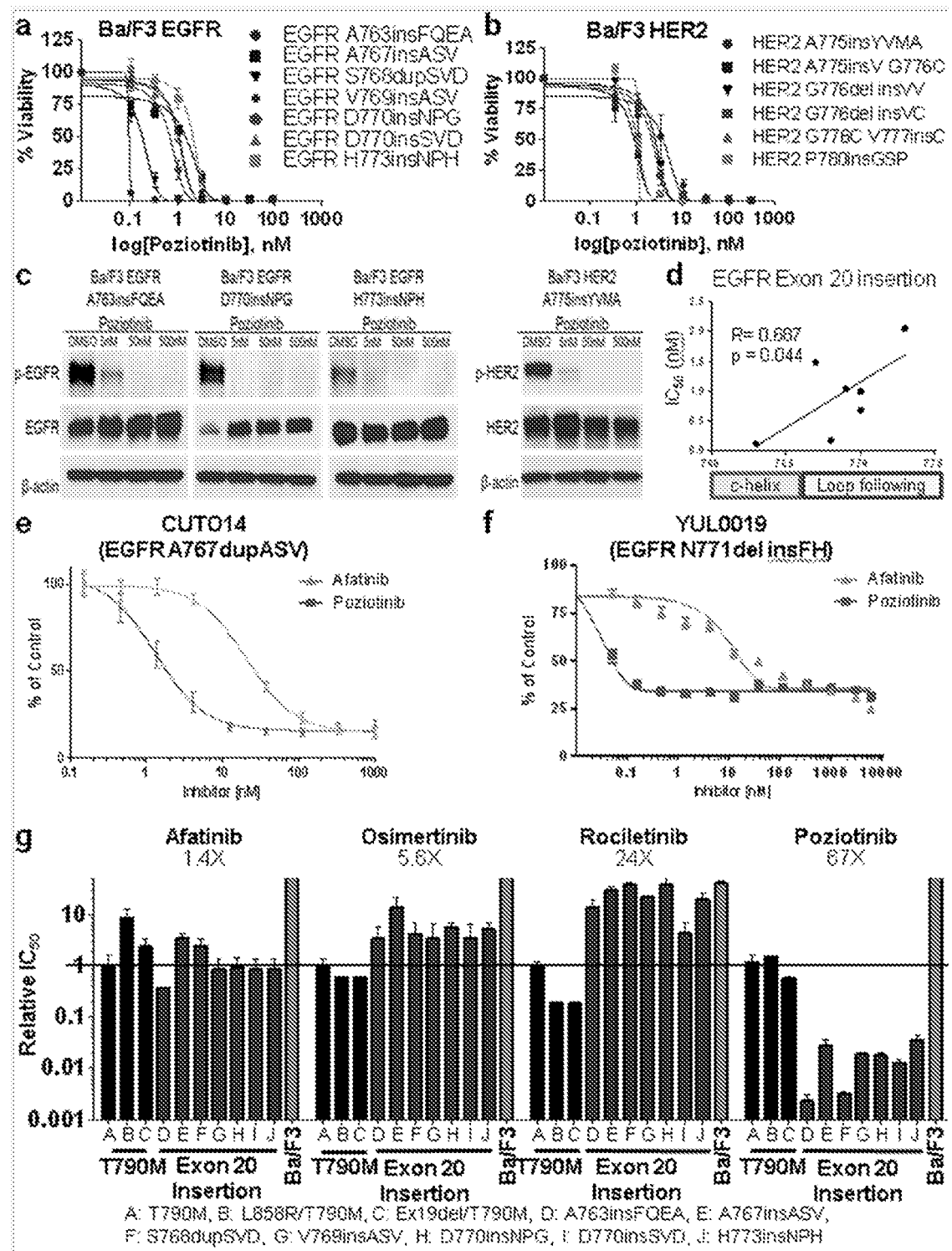
FIGS. 2A-2G: Poziotinib potently inhibits EGFR and HER2 exon 20 insertion mutations. Dose response curves of cell viability of Ba/F3 cell lines expressing EGFR (FIG. 2A) and HER2 (FIG. 2B) exon 20 insertion mutations treated with poziotinib for 72 hours. The mean±SEM of each individual cell line is plotted for each concentration (n=3).
Figures 8A, 8B, 8C, 8D, 8E:
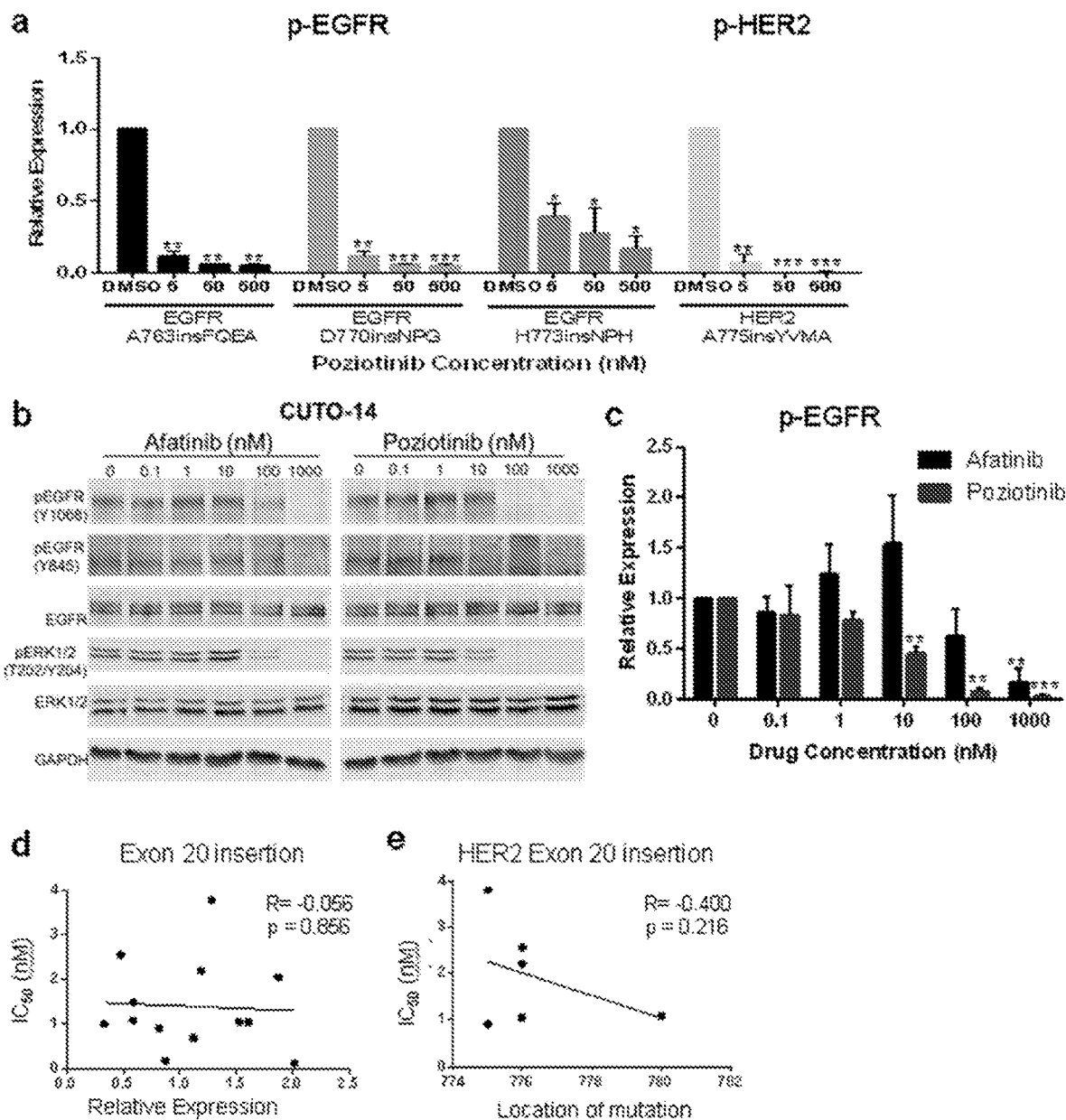
FIGS. 8A-8E: EGFR and HER2 exon 20 insertions mutations are sensitive to poziotinib in vitro.
Figure 9:
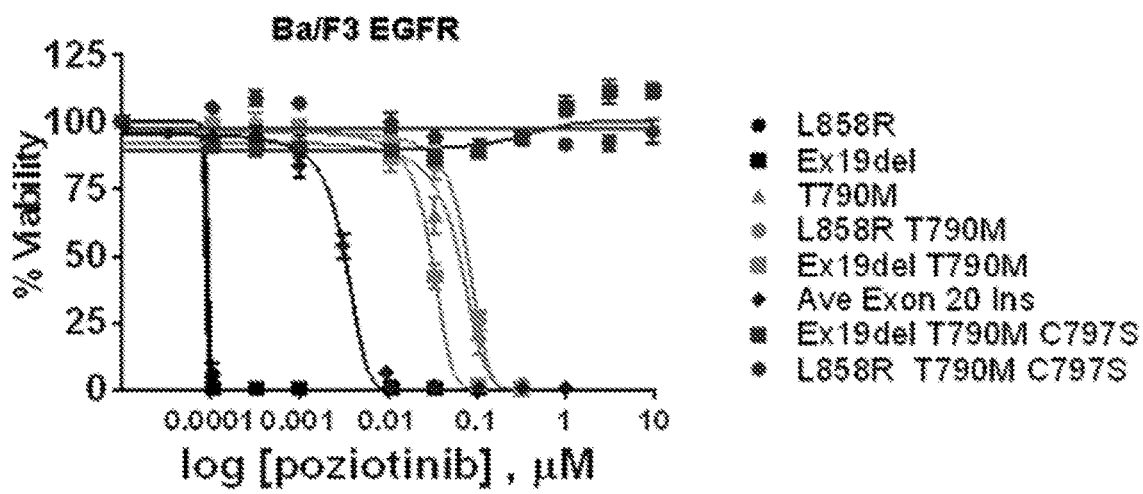
FIG. 9: C797S and EMT are two distinct mechanisms of poziotinib resistance in vitro. Dose response curves of cell viability of EGFR mutant Ba/F3 cell lines treated with poziotinib for 72 hours. The mean±SEM is plotted for each concentration (n=3).

It was next sought to identify TKIs with enhanced activity against exon 20 insertions. Poziotinib, like afatinib, also contains a small terminal group and a flexible quinazoline core. However, poziotinib has smaller substituent groups linking the Michael Acceptor group to the quinazoline core compared to afatinib and increased halogenation of the terminal benzene ring compared to afatinib. This electron-rich moiety also interacts with basic residues of EGFR such as K745 to further stabilize its binding. Therefore, poziotinib was tested in the Ba/F3 system. In vitro, poziotinib potently inhibited the growth of EGFR exon 20 mutant Ba/F3 cell lines (FIG. 2A) and HER2 exon 20 mutant Ba/F3 cells (FIG. 2B). Poziotinib had an average $IC_{50}$ value of 1.0 nM in EGFR exon 20 mutant Ba/F3 cell lines making poziotinib approximately 100 times more potent than osimertinib and 40 times more potent than afatinib in vitro. Moreover, poziotinib had an average $IC_{50}$ value of 1.9 nM in HER2 exon 20 mutant Ba/F3 cell lines, making poziotinib 200 times more potent than osimertinib and 6 times more potent than afatinib in vitro. These results were validated by western blotting where poziotinib inhibited phosphorylation of EGFR and HER2 at concentrations as low as 5 nM (FIGS. 2C, 8A). Furthermore, to validate that poziotinib sensitivity was not due to level of expression of EGFR or HER2 mutants, expression of each mutant was determined by ELISA then plotted against $IC_{50}$ values (FIG. 8D). While no correlation was found between $IC_{50}$ and expression (R= −0.056, p=0.856), a correlation was found between poziotinib sensitivity and location of the mutation for EGFR (R=0.687, p=0.044) (FIG. 2D), suggesting that the further away the insertion is from the α-c-helix, the higher the $IC_{50}$. Interestingly, this correlation was not found for HER2 exon 20 mutations which vary more in the size of the insertion rather than the location (FIG. 8E). This correlation suggests that the precise location of the mutation has varying effects on the drug binding pocket, contributing to the heterogeneity of drug response seen. In addition, poziotinib effectively inhibited growth of patient derived cell lines CUTO14 (EGFR A767dupASV) and YUL0019 (EGFR N771del insFH) with an average $IC_{50}$ value of 1.84 nM and 0.30 nM, respectively, which was 15 times more potent than afatinib for CUTO14 and more than 100 times more potent than afatinib for YUL0019 (FIG. 2E, F). Western blotting of CUTO14 cell line determined that there was significant inhibition of p-EGFR at 10 nM poziotinib treatment but p-EGFR was not significantly inhibited by afatinib until 1000 nM (FIG. 8B, C).

To determine the specificity of poziotinib to inhibit exon 20 mutants compared to T790M mutants, the $IC_{50}$ values of afatinib, osimertinib, rociletinib, and poziotinib were compared in exon 20 mutants to the $IC_{50}$ values of afatinib, osimertinib, rociletinib, and poziotinib in EGFR T790M mutant Ba/F3 cell lines. $IC_{50}$ values are displayed normalized to the single EGFR T790M mutation, where values less than 1 indicate specificity to exon 20 insertions compared to T790M (FIG. 2G). When compared to EGFR T790M mutants, EGFR exon 20 insertions were 65 times more sensitive to poziotinib. Moreover, EGFR exon 20 insertion mutations were 1.4 times more resistant to afatinib, 5.6 times more resistant to osimertinib, and 24 times more resistant to rociletinib than EGFR T790M mutants (FIG. 2G).

To examine why poziotinib, but not third generation TKIs such as osimertinib, selectively and potently inhibits exon 20 mutants compared to T790M mutations, 3-D modeling was performed to determine how changes in the drug binding pocket affect drug binding. While osimertinib fits into the drug binding pocket of EGFR T790M mutant receptor (FIG. 2H), in exon 20 mutants, large changes (FIG. 2I) within the binding pocket sterically hinder the binding of third generation inhibitors. However, poziotinib is smaller and has greater flexibility allowing it to fit into the sterically hindered exon 20 binding pocket (FIG. 2I). Moreover, 3-D modeling of EGFR D770insNPG with poziotinib and afatinib suggest that the shifted P-loop into the drug binding pocket causes poziotinib to bind more tightly into the drug binding pocket than afatinib. Calculations of structural modeling indicate that the free energy of binding (London AG) for poziotinib is lower than afatinib, indicating stronger binding affinity of poziotinib. 3-D modeling of WT HER2 with osimertinib demonstrates that the binding pocket of WT HER2 is larger than the binding pocket of HER2 A775insYVMA. Thus, poziotinib tightly binds deep into the sterically hindered drug binding pocket of HER2 A775insYVMA overcoming structural changes induced by exon 20 insertions.

Figures 3A, 3B, 3C, 3D, 3E, 3F, 3G, 3H:
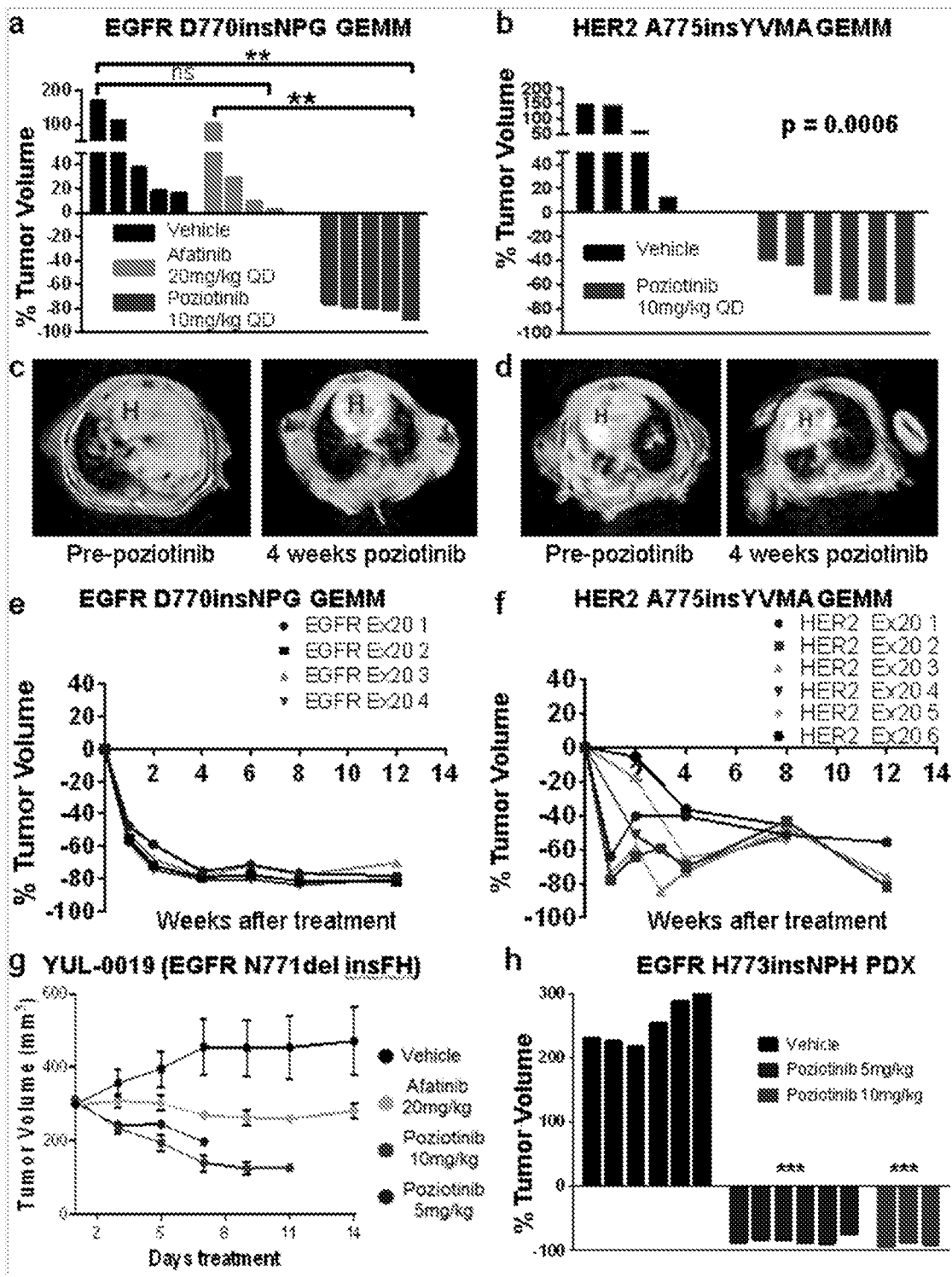
FIGS. 3A-3H: Poziotinib reduces tumor burden in EGFR and HER2 exon 20 insertion mutation mouse models. EGFR D770insNPG (FIG. 3A) or HER2 A775insYVMA (FIG. 3B) mice were treated daily with vehicle (EGFR n=5 and HER2 n=4), 20 mg/kg of afatinib (EGFR n=4), or 10 mg/kg of poziotinib (EGFR n=5 and HER2 n=6) for 4 weeks. Waterfall plots of tumor volume change as measured by MRI demonstrate 85% and 60% tumor inhibition with poziotinib at 4 weeks in EGFR and HER2 GEMMs, respectively.

The efficacy of poziotinib was tested in vivo using GEM models of EGFR and HER2 exon 20 insertion-driven NSCLC. Lung tumors were induced in previously described EGFR D770insNPG (Cho et al., 2013) and HER2 A775insYVMA (Perera et al., 2009) mice, and animals orally received poziotinib (10 mg/kg) or vehicle daily control for 4 weeks. As determined by MRI, Poziotinib reduced tumor burden by 85% in EGFR exon 20 GEMMs (FIG. 3A,C) and 60% in HER2 exon 20 GEMMs (FIG. 3B, D), a higher level of inhibition than the 37% previously observed for afatinib in the identical GEM model. Representative MRI images of tumors before and after poziotinib are shown for both EGFR and HER2 GEMMs (FIG. 3C, D). In both EGFR and HER2 GEM models, mice treated with 10 mg/kg poziotinib demonstrated durable regression, without signs of progression at 12 weeks (FIG. 3E, F). In addition, poziotinib treatment (5 or 10 mg/kg) completely reduced tumors by 14 days (>85% inhibition) in EGFR exon 20 insertions PDX model LU0387 (H773insNPH) (FIG. 3G).

To determine if poziotinib, like other irreversible inhibitors, binds covalently at C797, Ba/F3 cell lines were generated with the C797S mutation observed in ~30% of patients with osimertinib resistance (Thress et al., 2015). It was found that the C797S mutation induced resistance to poziotinib with $IC_{50}$ value of >10 µM. Together these experiments suggested that poziotinib may be susceptible to similar mechanisms of acquired resistance as other third generation TKIs.

Figure 10:
FIG. 10: Dose response curves of cell viability of MCF10A HER2 G776del insVC cell line treated with indicated TKIs.

To validate the above findings, experiments were performed using a breast cancer cell line MCF10A with a HER2 G776del insVC. The cells were treated with the different inhibitors at varying doses, and it was found that the breast cancer cell line is sensitive to poziotinib as seen in the other cell lines tested (FIG. 10). Therefore, poziotinib can be used for the treatment of other cancers with exon 20 mutations.

Thus, it was found that exon 20 mutants exhibit de novo resistance to first, second, and third generation TKIs. Using 3-D modeling of EGFR D770insNPG and HER2 A775insYVMA poziotinib was identified as having structural features that could overcome changes within the drug binding pocket induced by insertions in exon 20. Moreover, the predicted activity of poziotinib was confirmed using in vitro and in vivo models demonstrating the potent antitumor activity of poziotinib in cells with these mutations.

Poziotinib was found to be approximately 40 times more potent than afatinib and 65 times more potent than dacomitinib in EGFR exon 20 mutants. Moreover, poziotinib was 6 times more potent that afatinib and dacomitinib in HER2 exon 20 mutants in vitro. Taken together, these data indicate that although poziotinib shares a similar quinazoline backbone with afatinib and dacomitinib, additional features of the kinase inhibitor result in increased activity and relative specificity for EGFR exon 20 mutations compared with the more common T790M mutation.

The 3-D modeling suggests that the smaller size, increased halogenation, and flexibility of poziotinib give the inhibitor a competitive advantage in the sterically hindered drug binding pocket of exon 20 mutant EGFR/HER2. A negative correlation was observed between the distance of the mutation from the α-c-helix and drug sensitivity. This relationship suggests that the precise location of the mutation affects the drug binding pocket and/or binding affinity of the TKI. Furthermore, the data indicated that the size of the insertion also affects drug sensitivity. Furthermore, the patient derived cell line, YUL0019 (N771del insFH) which had a net gain of only one amino acid, was more sensitive to quinazoline based pan-HER inhibitors than cell lines with larger EGFR exon 20 insertions.

Example 2

Materials and Methods

Patient population and statistical analyses: Patients with EGFR mutant NSCLC enrolled in the prospectively collected MD Anderson Lung Cancer Moon Shot GEMINI database were identified. EGFR mutation status was determined using one of PCR-based next generation sequencing of panels of 50, 134 or 409 genes used for routine clinical care. PFS was calculated using the Kaplan Meier method. PFS was defined as time from commencement of EGFR TKI to radiologic progression or death. Restaging scans were obtained at 6-8 week intervals during treatment and were retrospectively assessed according to the Response Evaluation Criteria in Solid Tumors (RECIST), version 1.1 to determine response rate in patients with EGFR exon 20 insertion NSCLC.

Cell line generation and IL-3 deprivation: Ba/F3 cell line, was cultured in complete RPMI-1640 (R8758; Sigma Life Science) media supplemented with L-glutamine, 10% heat inactivated FBS (Gibco), 1% penicillin/streptomycin (Sigma Life Science), and 10 ng/ml mouse IL-3 (R&D systems) under sterile conditions. Stable cell lines were generated by retroviral transduction of Ba/F3 cell line for 12 hours. Retroviruses were generated by transfecting pBabe-Puro based vectors summarized in Table 2 (Addgene and Bioinnovatise) into the Phoenix 293T ampho packing cell line (Orbigen) using Lipofectamine 2000 (Invitrogen). 72 hours after transduction, 2 µg/ml puromycin (Invitrogen) was added to the media. After 5 days of selection, cells were stained with FITC-HER2 (Biolegend) or PE-EGFR (Biolegend) and sorted via FACS. Cell lines were then grown in the absence of IL-3 for 15 days and cell viability was determined every 3 days using the Cell Titer Glo assay (Progema). Resulting stable cell lines were maintained in complete RPMI-1640 media described above without IL-3. HCC827 and HCC4006 lung cancer cell lines were obtained from ATCC and maintained in 10% RPMI media under sterile conditions. Cell line identity was confirmed by DNA fingerprinting via short tandem repeats using the PowerPlex 1.2 kit (Promega). Fingerprinting results were compared with reference fingerprints maintained by the primary source of the cell line. All cell lines were free of mycoplasma. To generate erlotinib resistant cell lines, HCC827 and HCC4006 (both EGFR mutant) cells were cultured with increasing concentrations of erlotinib until resistant variants emerged.

TABLE 2

Vector used to generate stable cell lines.

| Name | Mutation | Vendor |
|---|---|---|
| EGFR A763insFQEA (SEQ ID NO: 1) | c.2290_2291insTCCAGGAAGCCT (SEQ ID NO: 2) | Created from Bioinnovatise from pBabe-puro-EGFR WT from Addgene (#11011) |
| EGFR A767insASV | c.2302_2303insGCCAGCGTG | Purchased from Addgene (#32066) |
| EGFR S768dupSVD | c.2303_2304dupAGCGTGGAC | Created from Bioinnovatise from pBabe-puro-EGFR WT from Addgene (#11011) |
| EGFR V769insASV | c.2308_2309insCCAGCGTGG | Created from Bioinnovatise from pBabe-puro-EGFR WT from Addgene (#11011) |
| EGFR D770insNPG | c.2310_2311insAACCCCGGC | Purchased from Addgene (#11016) |
| EGFR D770insSVD | c.2311_2312insGCGTGGACA | Created from Bioinnovatise from pBabe-puro-EGFR WT from Addgene (#11011) |
| EGFR H773insNPH | c.2319_2320insAACCCCCAC | Created from Bioinnovatise from pBabe-puro-EGFR WT from Addgene (#11011) |
| EGFR T790M | | Purchased from Addgene (#32070) |
| EGFR T790M L858R | | Purchased from Addgene (#32073) |
| EGFR T790M Ex19del | | Purchased from Addgene (#32072) |
| EGFR T790M L858R C797S | c.2389T > A | Created from Bioinnovatise from pBabe-puro-EGFR L858R/T790M from Addgene (#32073) |
| EGFR T790M Ex19del C797S | c.2389T > A | Created from Bioinnovatise from pBabe-puro-EGFR Del1/T790M from Addgene (#32072) |
| HER2 S310F | c.929C > T | Purchased from Addgene (#40991) |
| HER2 S310Y | c.929C > A | Purchased from Addgene (#40992) |
| HER2 C311R | c.931T > C | Purchased from Addgene (#40980) |
| HER2 L755P | c.2263_2264delinsCC | Created by Bioinnovatise from pBabe-puro HER2 WT from Addgene (#40978) |
| HER2 A775insV G776C | c.2323_2324insTTT | Purchased from Addgene (#40979) |
| HER2 A775insYVMA (SEQ ID NO: 3) | c.2323_2324insTATGTCATGGCT (SEQ ID NO: 4) | Purchased from Addgene (#40982) |
| HER2 G776V | c.2327G > T | Created by Bioinnovatise from pBabe-puro HER2 WT from Addgene (#40978) |
| HER2 G776C V777insV | c.2326G > T, c.2331_2332insTGT | Created by Bioinnovatise from pBabe-puro HER2 WT from Addgene (#40978) |
| HER2 G776del insVV | c.2327delinsTTGT | Created by Bioinnovatise from pBabe-puro HER2 WT from Addgene (#40978) |
| HER2 G776del insVC | c.2326_2328insTCT | Created by Bioinnovatise from pBabe-puro HER2 WT from Addgene (#40978) |
| HER2 P780insGSP | c.2339_2340insTGGCTCCCC | Created by Bioinnovatise from pBabe-puro HER2 WT from Addgene (#40978) |

Cell Viability Assay and $IC_{50}$ Estimation: Cell viability was determined using the Cell Titer Glo assay (Promega). Cells were collected from suspension media, spun down at 300×g for 5 minutes and re-suspended in fresh RPMI media and counted using a Countess automated cell counter and trypan blue (Invitrogen). 1500 cells per well were plated in 384-well plates (Greiner Bio-One) in technical triplicate. Cells were treated with seven different concentrations of inhibitors in serial three-fold diluted TKIs or vehicle alone at a final volume of 40 µL per well. After 72 hours, 11 µL of Cell Titer Glo was added to each well. Plates were shaken for 10 minutes, and bioluminescence was determined using a FLUOstar OPTIMA multi-mode micro-plate reader (BMG LABTECH). Bioluminescence values were normalized to DMSO treated cells, and normalized values were plotted in GraphPad Prism using non-linear regression fit to normalized data with a variable slope. $IC_{50}$ values were calculated by GraphPad Prism at 50% inhibition. Each experiment was replicated 3 times unless indicated.

Tyrosine Kinase Inhibitors: Lapatinib, afatinib, dacomitinib, AZD9291, CO-1686, EGF816, ibrutinib, and HM781-36B were purchased from Selleck Chemical. Erlotinib and gefitinib were obtained from the institutional pharmacy at The University of Texas MD Anderson Cancer Center. BI-694 was provided by Boehringer-Ingelheim. All inhibitors were dissolved in DMSO at a concentration of 10 mM and stored at −80° C.

3-D modeling: The structure of EGFR D770insNPG protein was retrieved (Protein Data Bank entry code: 4LRM) and used it as a template to build our molecular 3-D structural model of EGFR D770insNPG. HER2 A775insYVMA was built using the previously published model in Shen et al. The homology models were built using MODELLER 9v6 and further energetically minimized using Molecular Operating Environment software package (Chemical Computing Group, Montreal, Canada). Molecular docking of TKIs into exon 20 mutant EGFR and HER2 were performed using GOLD software with default parameters unless otherwise noted. No early termination was allowed in the docking process. Restraints were used to model the covalent bond formations between receptors and inhibitors. The flexibility of residues within the binding pocket was addressed using GOLD software. Figures demonstrating interactions between EGFR/HER2 and inhibitors were visualized using PYMOL.

Western Blotting of Ba/F3 mutants: For Western blotting, cells were washed in phosphate-buffered saline and lysed in protein lysis buffer (ThermoFisher) and protease inhibitor cocktail tablets (Roche). Protein (30-40 µg) was loaded into gels purchased from BioRad. BioRad semi-dry transfer was used and then probed with antibodies against pEGFR (#2234), EGFR (#4267), pHER2 (#2247), HER2 (#4290) (1:1000; Cell Signaling). Blots were probed with antibodies against β-actin (Sigma-Aldrich, #A2228) or vinculin (Sigma-Aldrich, #V4505) as a loading control, and exposed using SuperSignal West Pico Chemiluminescent Substrate (ThermoFisher) and BioRad's ChemiDoc Touch Imaging System or radiographic film. Representative images are shown of two separate protein isolations and blots run in duplicate. Quantification of western blotting was completed in Photoshop and calculated as (background mean intensity−sample mean intensity) (number of pixels)=band intensity. Samples were normalized first to loading control (β-actin or vinculin), then normalized to DMSO and graphed in GraphPad Prism. Significance from DMSO was calculated in GraphPad Prism.

ELISA and correlation of Ba/F3 mutants: Protein was harvested from the parental Ba/F3 cell line and each of the Ba/F3 exon 20 mutants found to be activating mutations as described above. ELISA was performed as described by the manufacture instructions for total EGFR (Cell signaling, #7250) and total HER2 (Cell Signaling, #7310). Relative expression determined by ELISA was plotted against $IC_{50}$ values calculated as described above. Pearson correlations and p-values were determined by GraphPad Prism.

Patient Derived Cell line studies: CUTO14 cells were generated from the pleural effusion of a patient with lung adenocarcinoma following informed consent using previously described culture methods (Davies et al., 2013). Cell lines were treated with the indicated doses of afatinib or poziotinib for 72 hours and cell viability was determined by MTS assay (Promega). IC50 was calculated as previously described (n=3). Western blotting with patient derived cell lines was completed as previously described (Hong et al., 2007) (n=3). Cells were treated for 2 hours with indicated doses of afatinib or poziotinib. All antibodies were purchased from Cell Signaling Technology with the exception of total EGFR (BD Transduction Laboratories) and GAPDH (Calbiochem).

The YUL0019 cell line was established from malignant pericardial fluid obtained from a patient with advanced adenocarcinoma of the lung under an IRB-approved protocol. The cell line was cultured in RPMI+L-glutamine (Corning), supplemented with 10% heat-inactivated fetal bovine serum (Atlanta Biologicals) and 1% penicillin/streptomycin (Corning). To confirm the presence of the EGFR mutation, RNA was extracted from cell pellet using the RNeasy mini kit (Qiagen #74104) according to manufacturer's instructions. cDNA was synthesized using the Superscript III First-Strand cDNA Synthesis Kit (Invitrogen #18080-051) and used as a template to amplify EGFR. PCR product was sequenced by Sanger sequencing using the following primers: EGFR-2080F: CTTACACCC AGTGGAGAAGC (SEQ ID NO:5) and EGFR-2507R ACCAAGCGACGGTCCTC-CAA (SEQ ID NO:6). Forward and reverse sequence tracings were manually reviewed. The variant detected in the patient-derived cell line was a complex insertion in exon 20 of EGFR (N77 1delinsFH) leading to the replacement of amino acid asparagine at position 771 by two amino acids, phenylalanine and histidine. Cell viability and $IC_{50}$ estimation was performed as described above.

Patient Derived Xenograft (PDX) studies: LU0387 PDX experiments were completed by Crown BioSciences. Briefly, tumor fragments from EGFR H773insNPH expressing tumors were inoculated into 5-6 week old female nu/nu nude mice. When tumors reached 100-200 mm$^3$ mice were randomized into 3 groups: 5 mg/kg poziotinib, 10 mg/kg poziotinib, or vehicle control (20% PEG-400, 3% Tween-80 in dH$_2$O). Tumor volumes and body weight were measured twice weekly. Mice receiving 5 mg/kg poziotinib received drug for 4-5 days then were on dosing holiday for 4 days then received 4 additional days of dosing. Mice were then observed for 2 additional days without dosing. Mice receiving 10 mg/kg poziotinib received drug for 3-4 days then were observed for 10 days without dosing. Mice humanly euthanized for events unrelated to tumor burden were excluded from final analysis.

Genetically Engineered Mouse Model (GEMM) studies: EGFR D770insNPG and HER2 A775insYVMA GEMMs were generated as previously described (Perera et al., 2009; Cho et al., 2013). Mice were handled in accordance with Good Animal Practices as defined by the Office of Laboratory Animal Welfare and done in with approval from Dana- Farber Cancer Institute Institutional Animal Care and Use Committee (Boston, Mass.). Mice were fed a continuous doxycycline diet from 6 weeks of age. Tumor volume was determined by MRI as previously described (Perera et al., 2009; Cho et al., 2013). Mice with equal initial tumor volume were non-blindly randomized to vehicle and 10 mg/kg poziotinib daily upon obvious tumor formation determined by MRI. Mice humanly euthanized for events unrelated to tumor burden were excluded from final analysis.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Arcila et al., *Clin Cancer Res* 18:4910-8, 2012.
Arcila et al., *Mol Cancer Ther* 12(2):220-229, 2013.
Austin-Ward and Villaseca, *Revista Medica de Chile*, 126 (7):838-845, 1998.
Ausubel et al., Current Protocols in Molecular Biology, John Wiley & Sons, New York, N.Y., 2003.
Bukowski et al., *Clinical Cancer Res.*, 4(10):2337-2347, 1998.
Camacho et al. *J Clin Oncology* 22(145): Abstract No. 2505 (antibody CP-675206), 2004.
Cha et al. *Int J Cancer* 130:2445-54, 2012.
Chee et al., *Science*, 274:610-614, 1996.
Cho et al., *Cancer Res* 73:6770-9, 2013.
Christodoulides et al., *Microbiology*, 144(Pt 11):3027-3037, 1998.
Church and Gilbert, *Proc. Natl. Acad. Sci. USA* 81:1991-1995 (1988).
Cotton et al., *Proc. Natl. Acad. Sci. USA* 85:4397-4401 (1985).
Davidson et al., *J. Immunother.*, 21(5):389-398, 1998.
Davies et al., *Plos One* 8, 2013.
Del Tito et al., *Clinical Chemistry* 44:731-739, 1998.
Drmanac et al., *Nat. Biotechnol.*, 16:54-58, 1998.
Drmanac et al., *Science*, 260:1649-1652, 1993.
Flavell et al., *Cell* 15:25 (1978).
Fu et al., *Nat. Biotechnol.*, 16:381-384, 1998/
Geever et al., *Proc. Natl. Acad. Sci. USA* 78:5081 (1981).
Hanibuchi et al., *Int. J. Cancer,* 78(4):480-485, 1998.
Hellstrand et al., *Acta Oncologica*, 37(4):347-353, 1998.
Hollander, *Front. Immun.*, 3:3, 2012.
Hong et al., *J Biol Chem* 282:19781-7, 2007.
Hui and Hashimoto, *Infection Immun.*, 66(11):5329-5336, 1998.
Hurwitz et al. *Proc Natl Acad Sci USA* 95(17): 10067-10071, 1998.
International Patent Publication No. WO 99/57318
International Patent Publication No. WO1995001994
International Patent Publication No. WO1998042752
International Patent Publication No. WO2000037504
International Patent Publication No. WO2001014424
International Patent Publication No. WO2009/101611
International Patent Publication No. WO2009/114335
International Patent Publication No. WO2010/027827
International Patent Publication No. WO2011/066342
International Patent Publication No. WO2015016718
International Patent Publication No. WO 00/37504
International Patent Publication No. WO01/14424
International Patent Publication No. WO98/42752
Kosaka et al., *Cancer Res* 2017.
Leal, M., *Ann NY Acad Sci* 1321, 41-54, 2014.
Lynch et al., *N Engl J Med.* 350(21):2129-2139, 2004.
Maemondo et al., *N Engl J Med* 362:2380-8, 2010.
Mitsudomi and Yatabe, *Cancer Sci.* 98(12):1817-1824, 2007.
Mokyr et al. *Cancer Res* 58:5301-5304, 1998.
Oxnard et al., *J Thorac Oncol.* 8(2):179-184, 2013.
Paez et al., *Science* 304(5676):1497-1500, 2004.
Pao et al., *Proc Natl Acad Sci USA* 101(36):13306-13311, 2004.
Pardoll, *Nat Rev Cancer,* 12(4): 252-64, 2012.
Perera et al., *Proc Nat. Acad Sci USA* 106:474-9, 2009.
Qin et al., *Proc. Natl. Acad. Sci. USA,* 95(24):14411-14416, 1998.
Raca et al., *Genet Test* 8(4):387-94 (2004).
Sanger et al., *Proc. Natl. Acad. Sci. USA* 74:5463-5467 (1977).
Sears et al., *Biotechniques,* 13:626-633, 1992.
Sheffield et al., *Proc. Natl. Acad. Sci. USA* 86:232-236 (1989).
Shen et al., *J Recept Signal Transduct Res* 36:89-97, 2016.
Thress et al., *Nat Med* 21:560-2, 2015.
U.S. Pat. No. 4,870,287
U.S. Pat. No. 5,288,644
U.S. Pat. No. 5,739,169
U.S. Pat. No. 5,760,395
U.S. Pat. No. 5,801,005
U.S. Pat. No. 5,824,311
U.S. Pat. No. 5,830,880
U.S. Pat. No. 5,844,905
U.S. Pat. No. 5,846,945
U.S. Pat. No. 5,869,245
U.S. Pat. No. 5,885,796
U.S. Pat. No. 6,207,156
U.S. Pat. No. 8,008,449
U.S. Pat. No. 8,017,114
U.S. Pat. No. 8,119,129
U.S. Pat. No. 8,188,102
U.S. Pat. No. 8,329,867
U.S. Pat. No. 8,354,509
U.S. Pat. No. 8,735,553
U.S. Patent Publication No. 2004/0014095
U.S. Patent Publication No. 2005/0260186
U.S. Patent Publication No. 2006/0104968
U.S. Patent Publication No. 20110008369
U.S. Patent Publication No. 20130071452
U.S. Patent Publication No. 2014022021
U.S. Patent Publication No. 20140294898
Underhill et al., *Genome Res.* 7:996-1005 (1997).
Yang et al., *Int J Cancer* 2016.
Yasuda et al., *Sci Transl Med* 5(216):216ra177, 2013.
Zimmerman et al., *Methods Mol. Cell. Biol.*, 3:39-42, 1992.

What is claimed is:

1. A method of treating cancer in a subject comprising administering an effective amount of poziotinib to the subject, wherein the subject has a tumor that has been determined to have one or more EGFR exon 20 insertion mutations, wherein the mutations comprise an insertion of 1-6 amino acids between amino acids 763-778.

2. The method of claim 1, wherein the subject has been determined to have 2, 3, or 4 EGFR exon 20 insertion mutations.

3. The method of claim 1, wherein the one or more EGFR exon 20 insertion mutations are at one or more residues selected from the group consisting of A763, A767, S768, V769, D770, N771, P772, and H773.

4. The method of claim 1, wherein the subject has been determined to not have a C797 or T790M EGFR mutation.

5. The method of claim 1, wherein the one or more exon 20 insertion mutations are selected from the group consisting of A763insFQEA, A767insASV, S768dupSVD, V769insASV, D770insSVD, D770insNPG, H773insNPH, N771del insGY, N771del insFH, and N771dupNPH.

6. The method of claim 1, wherein the exon 20 insertion_mutation is D770insNPG.

7. The method of claim 1, further comprising administering an additional anti-cancer therapy.

8. The method of claim 7, wherein the additional anti-cancer therapy is chemotherapy, radiotherapy, gene therapy, surgery, hormonal therapy, anti-angiogenic therapy or immunotherapy.

9. The method of claim 7, wherein the poziotinib and/or anti-cancer therapy are administered intravenously, subcutaneously, intraosseously, orally, transdermally, in sustained release, in controlled release, in delayed release, as a suppository, or sublingually.

10. The method of claim 7, wherein the poziotinib and/or anti-cancer therapy are administered daily.

11. The method of claim 7, wherein the additional anti-cancer therapy is an mTOR inhibitor.

12. The method of claim 11, wherein the mTOR inhibitor is selected from the group consisting of rapamycin, temsirolimus, everolimus, ridaforolimus and MLN4924.

13. The method of claim 11, wherein the mTOR inhibitor is everolimus.

14. The method of claim 7, wherein the additional anti-cancer therapy is trastuzumab emtansine.

15. The method of claim 1, wherein the cancer is non-small cell lung cancer, oral cancer, oropharyngeal cancer, nasopharyngeal cancer, respiratory cancer, urogenital cancer, gastrointestinal cancer, central or peripheral nervous system tissue cancer, an endocrine or neuroendocrine cancer or hematopoietic cancer, glioma, sarcoma, carcinoma, lymphoma, melanoma, fibroma, meningioma, brain cancer, oropharyngeal cancer, nasopharyngeal cancer, renal cancer, biliary cancer, pheochromocytoma, pancreatic islet cell cancer, Li-Fraumeni tumors, thyroid cancer, parathyroid cancer, pituitary tumors, adrenal gland tumors, osteogenic sarcoma tumors, multiple neuroendocrine type I and type II tumors, breast cancer, lung cancer, head and neck cancer, prostate cancer, esophageal cancer, tracheal cancer, liver cancer, bladder cancer, stomach cancer, pancreatic cancer, ovarian cancer, uterine cancer, cervical cancer, testicular cancer, colon cancer, rectal cancer or skin cancer.

16. The method of claim 1, wherein the exon 20 insertion mutation is V769insASV.

17. The method of claim 1, wherein the exon 20 insertion mutation is A763insFQEA.

18. The method of claim 1, wherein the exon 20 insertion mutation is D770insSVD.

* * * * *